US012559611B2

(12) United States Patent
Hayakawa et al.

(10) Patent No.: US 12,559,611 B2
(45) Date of Patent: Feb. 24, 2026

(54) HYDROPHOBIC ALGINIC ACID PARTICLE GROUP AND METHOD FOR PRODUCING SAME

(71) Applicant: Nisshinbo Holdings Inc., Tokyo (JP)

(72) Inventors: Kazutoshi Hayakawa, Chiba (JP); Toshifumi Hashiba, Chiba (JP); Erina Matsuzaka, Chiba (JP)

(73) Assignee: NISSHINBO HOLDINGS INC., Tokyo (JP)

( * ) Notice: Subject to any disclaimer, the term of this patent is extended or adjusted under 35 U.S.C. 154(b) by 983 days.

(21) Appl. No.: 17/426,810

(22) PCT Filed: Jan. 30, 2020

(86) PCT No.: PCT/JP2020/003360
§ 371 (c)(1),
(2) Date: Jul. 29, 2021

(87) PCT Pub. No.: WO2020/162303
PCT Pub. Date: Aug. 13, 2020

(65) Prior Publication Data
US 2022/0127435 A1 Apr. 28, 2022

(30) Foreign Application Priority Data
Feb. 4, 2019 (JP) ................................. 2019-018101

(51) Int. Cl.
| | |
|---|---|
| *C08L 5/04* | (2006.01) |
| *A61K 8/19* | (2006.01) |
| *A61K 8/73* | (2006.01) |
| *A61Q 19/00* | (2006.01) |
| *C08B 37/00* | (2006.01) |
| *C08J 5/18* | (2006.01) |
| *C09D 105/04* | (2006.01) |

(52) U.S. Cl.
CPC ..................................... *C08L 5/04* (2013.01); *A61K 8/19* (2013.01); *A61K 8/733* (2013.01); *A61Q 19/00* (2013.01); *C08B 37/0084* (2013.01); *C08J 5/18* (2013.01); *C09D 105/04* (2013.01); *C08J 2305/04* (2013.01)

(58) Field of Classification Search
CPC ................................. A61K 8/733; C08L 5/04
See application file for complete search history.

(56) References Cited

U.S. PATENT DOCUMENTS

| | | | | |
|---|---|---|---|---|
| 5,843,417 A | * | 12/1998 | Hanna | ...................... A61Q 1/02 514/844 |
| 2008/0081029 A1 | | 4/2008 | Nishihama et al. | |
| 2009/0214719 A1 | | 8/2009 | Gouin et al. | |

FOREIGN PATENT DOCUMENTS

| | | | |
|---|---|---|---|
| CN | 106674555 A | * | 5/2017 |
| JP | 60-238139 A | | 11/1985 |
| JP | 9-175979 A | | 7/1997 |
| JP | 2002-284926 A | | 10/2002 |
| JP | 2005-272698 A | | 10/2005 |
| JP | 2006-131887 A | | 5/2006 |
| JP | 2009-501629 A | | 1/2009 |

OTHER PUBLICATIONS

Yuan et al. "Contact Angle and Wetting Properties" in Surface Science Techniques, Springer Series in Surface Sciences 51, Springer-Verlag Berlin Heidelberg, 2013 (Year: 2013).*
Smith "Mechanics of Absorption", Apr. 27, 2017, https://cleanfax.com/mechanics-of-absorption/ (accessed Aug. 5, 2024). (Year: 2017).*
Ching et al. "Alginate gel particles—A review of production techniques and physical properties" Critical Reviews in Food and Science Nutrition 2017, 57, 1133-1152. (Year: 2017).*
Sato et al., "Development of Fine Particles of Calcium Alginate and Application to Cosmetics", Sen'i to Kogyo, 1996, vol. 52, No. 1, pp. 20-26, cited in Specification, w/English translation (20 pages).
International Search Report dated Apr. 21, 2020, issued in counterpart International Application No. PCT/JP2020/003360 (3 pages).

* cited by examiner

*Primary Examiner* — Bethany P Barham
*Assistant Examiner* — Judith Marie Kamm
(74) *Attorney, Agent, or Firm* — WHDA, LLP

(57) ABSTRACT

The present invention provides a hydrophobic alginic acid particle group which is obtained by subjecting a polyvalent metal alginate to a hydrophobization treatment, and which is configured such that the water absorption per 100 g of the particles is lower than the oil absorption per 100 g of the particles.

13 Claims, 1 Drawing Sheet

HYDROPHOBIC ALGINIC ACID PARTICLE GROUP AND METHOD FOR PRODUCING SAME

TECHNICAL FIELD

The present invention relates to hydrophobic alginic acid particles and a method for producing the same.

BACKGROUND ART

Fine particles serve as an important material in key industries. Synthetic resins have been used up until now as a raw material for fine particles. However, environmental pollution (marine pollution) and adverse ecological impacts by microplastics have become serious problems in recent years, and so efforts are starting to be made to reduce the generation of microplastics.

Although there is interest in the use of naturally occurring polymers such as cellulose as a raw material for making fine particles, cellulose readily absorbs water and has a relatively high swellability. A high swellability is not desirable from the standpoint of dimensional stability and also the tactile feel and moldability. Moreover, even though cellulose has a high degradability on land such as in the soil, the solubility and decomposability of cellulose in the marine environment are low.

Alginic acid is a polymer derived from seaweed. Because it is broken down by marine microorganisms and also by enzymes released from seaweeds, shellfish and the like, decomposition in the ocean is relatively rapid. However, it has an excessively high water absorbency, and so industrial use is limited.

As described in Non-Patent Document 1, by calcium-crosslinking alginic acid, the swellability can be suppressed, enabling the characteristics of alginic acid to be put to full use in cosmetics such as antiperspirants that require moisture absorbing and releasing properties, which is highly advantageous. On the other hand, in base makeup, point makeup and the like, when the humidity of outside air is high, the makeup readily absorbs moisture and thus tends to feel sticky depending on the weather, which may be unpleasant to some users. Also, calcium alginate particles have a high water absorbency; because the performance is high, they tend to cause makeup to run or smear. Moreover, when the water to absorbency is too high, the compatibility with oils in liquid foundations, makeup bases and the like is poor, which may limit the product formulations and uses.

Separately, in fields such as electrical materials that are averse to water absorption and moisture absorption, there is a risk of calcium alginate particles lowering performance, and so applications directed at industrial materials are limited. In light of environmental problems such as marine pollution, there exists a desire for a basic ingredient that is useful in industrial materials overall.

PRIOR ART DOCUMENTS

Non-Patent Documents

Non-Patent Document 1: Sato, T., et al.: "Development of calcium alginate fine particles and expansion of their use into cosmetics," Sen 'i to Kogyo, vol. 52, No. 1, pp. 20-26 (1996)

SUMMARY OF INVENTION

Technical Problem

The present invention was arrived at in light of the above circumstances. The object of this invention is to provide hydrophobic polymer particles made of a naturally occurring ingredient that can address the above desires.

Solution to Problem

The inventors have conducted extensive investigations in order to achieve the above object. As a result, they have discovered a method for hydrophobizing particles composed of crosslinked alginic acid such as calcium alginate. The inventors have also found that the hydrophobized alginic acid particles have an excellent water repellency and tactile feel and that although these particles are insoluble in water, they dissolve in seawater and are decomposed by microorganisms, making them useful as a measure for controlling marine pollution. These discoveries ultimately led to the present invention.

Accordingly, the invention provides the following hydrophobic alginic acid particles and methods for producing the same.

1. Hydrophobic alginic acid particles obtained by hydrophobizing a polyvalent metal salt of alginic acid, wherein the particles have a water absorption per 100 g of particles and an oil absorption per 100 g of particles such that the water absorption is lower than the oil absorption.

2. The hydrophobic alginic acid particles of 1 above, wherein hydrophobization is carried out using at least one hydrophobizing agent selected from the group consisting of carboxylic acids, amino acids and derivatives thereof, organosilicon compounds, silicone compounds, fluorine compounds, sulfate esters, sulfonic acids, phosphate esters, lactic acid esters, and salts thereof.

3. The hydrophobic alginic acid particles of 2 above, wherein the hydrophobizing agent is at least one selected from the group consisting of carboxylic acids, amino acids, organosilicon compounds, and salts thereof.

4. The hydrophobic alginic acid particles of 3 above, wherein the hydrophobizing agent is at least one selected from the group consisting of carboxylic acid salts and amino acid salts.

5. The hydrophobic alginic acid particles of any of 1 to 4 above, wherein the metal is a metal that forms divalent ions.

6. The hydrophobic alginic acid particles of 5 above, wherein the metal is calcium.

7. The hydrophobic alginic acid particles of any of 1 to 6 above which, at 25° C., are insoluble in water and are soluble in a 3 wt % aqueous solution of sodium chloride.

8. The hydrophobic alginic acid particles of any of 1 to 7 above which have an average particle size of 5 mm or less.

9. The hydrophobic alginic acid particles of any of 1 to 8 above wherein, letting SD1, SD2 and SD3 be the respective percent transmittances to 560 mu wavelength light of a dispersion prepared by dispersing the hydrophobic alginic acid particles in a 3 wt % aqueous solution of sodium chloride to a concentration of 0.1 wt % when 72 hours, 240 hours and 720 hours have elapsed following preparation, and letting WD1, WD2 and WD3 be the respective percent transmittances to 560 nm wavelength light of a dispersion prepared by dispersing the hydrophobic alginic acid particles in water to a concentration of 0.1 wt % to when 72 hours, 240 hours and 720 hours have elapsed following preparation, at least one of the ratios WD1/SD1, WD2/SD2 and WD3/SD3 is 0.9 or less.

10. A cosmetic which includes the hydrophobic alginic acid particles of any of 1 to 9 above.

11. A paint which includes the hydrophobic alginic acid particles of any of 1 to 9 above.

12. A resin composition which includes the hydrophobic alginic acid particles of any of 1 to 9 above.

13. A molded or formed article which includes the hydrophobic alginic acid particles of any of 1 to 9 above.

14. An electronic material which includes the hydrophobic alginic acid particles of any of 1 to 9 above.

15. A sheet which includes the hydrophobic alginic acid particles of any of 1 to 9 above.

16. A method of producing hydrophobic alginic acid particles, which method includes the step of hydrophobizing alginic acid particles containing a polyvalent metal salt of alginic acid.

17. A method of producing hydrophobic alginic acid particles, which method includes the steps of spray-drying a solution containing a monovalent salt of alginic acid and a hydrophobizing agent to obtain particles, and then crosslinking the particles using a polyvalent metal salt and at the same time hydrophobizing the particles.

18. A method of producing hydrophobic alginic acid particles, which method includes the steps of forming a water droplet-in-oil emulsion which contains a monovalent salt of alginic acid and a hydrophobizing agent in the water droplets, and then carrying out crosslinking treatment using a polyvalent metal salt and at the same time carrying out hydrophobization.

Advantageous Effects of Invention

The hydrophobic alginic acid particles of the invention, because they contain little foreign matter such as agglomerates and can be stably and efficiently produced, because they can be controlled to a small size and to a flattened or other shape, and also because crosslinkable particles having heat resistance and (hot) chemical resistance too can be stably produced, are capable of being employed in various applications. Moreover, given that the hydrophobic alginic acid particles of the invention are environmentally friendly particles which have an excellent water repellency and tactile feel, and in particular are natural polymer-derived particles that are useful as a measure for controlling marine pollution, they can be effectively employed in applications such as paints, inks, molded or formed articles, cosmetics and thermally cavitated molded or formed products for which, depending on the intended use, environmental measures are required.

DESCRIPTION OF EMBODIMENTS

[Hydrophobic Alginic Acid Particles]

Figure 1:
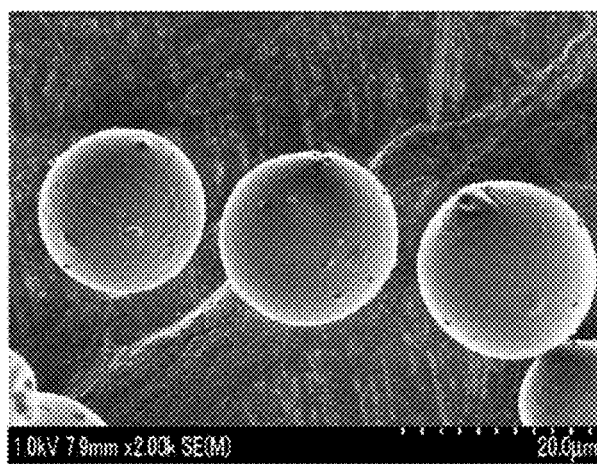
FIG. 1 shows a scanning electron micrograph (2,000×) of the particles obtained in Example 1-1.

The hydrophobic alginic acid particles of the invention are obtained by hydrophobizing particles of a polyvalent metal salt of alginic acid.

Examples of the polyvalent metal salt of alginic acid include, but are not particularly limited to, calcium alginate, strontium alginate, magnesium alginate, barium alginate, radium alginate, lead alginate, zinc alginate, nickel alginate, iron alginate, copper alginate, cadmium alginate, cobalt alginate and manganese alginate. Of these, from the standpoint of, for example, environmental concerns, safety, adjustment in the degree of crosslinking, versatility, cost and the like, calcium alginate is preferred.

The compound used in hydrophobization (also referred to below as the "hydrophobizing agent") is exemplified by carboxylic acids, amino acids and derivatives thereof, organosilicon compounds, silicone compounds, fluorine compounds, sulfate esters, sulfonic acids, phosphate esters, lactic acid esters, and salts of these. When designing the hydrophobizing agent so as to, out of environmental considerations, fully satisfy the to conditions of solubility in water and salt water and also degradability by microorganisms in the environment, one having a molecular weight of 5,000 or less is preferred, one having a molecular weight of from 50 to 1,000 is more preferred, one having a molecular weight of from 100 to 600 is even more preferred, and one having a molecular weight of from 200 to 500 is most preferred. In this invention, the molecular weight of a polymer refers to the number-average molecular weight (Mn), this being the polystyrene-equivalent value measured by gel permeation chromatography. For compounds other than polymers, the molecular weight refers to the chemical formula weight.

The carboxylic acid is preferably one having from 6 to 30 carbon atoms, more preferably one having from 8 to 25 carbon atoms, and most preferably one having from 10 to 20 carbon atoms. The carboxylic acid may be a monocarboxylic acid or a polycarboxylic acid.

Examples of monocarboxylic acids include caproic acid, enanthic acid, caprylic acid, octanoic acid, pelargonic acid, capric acid, undecylenic acid, lauric acid, myristic acid, pentadecanoic acid, palmitic acid, palmitic acid, palmitoleic acid, margaric acid, stearic acid, isostearic acid, oleic acid, vaccenic acid, ricinolic acid, linoleic acid, linolenic acid, eleostearic acid, oxystearic acid, arachidic acid, mead acid, arachidonic acid, eicosapentaenoic acid, behenic acid, docosahexaenoic acid, lignoceric acid, nervonic acid, cerotic acid, montanic acid, melissic acid, coconut oil fatty acid and palm oil fatty acid. Isomers of these having branched structures can also be used.

Examples of polycarboxylic acids include octanedioic acid, nonanedioic acid, decanedioic acid, undecanedioic acid, dodecanedioic acid, tridecanedioic acid, tetradecanedioic acid, peutadecanedioic acid, hexadecanedioic acid, heptadecanedioic acid, octadecanedioic acid, nouadecanedioic acid and eicosanedioic acid. Isomers of these having a branched structure, and polycarboxylic acids with a functionality of three or more can also be used.

The carboxylic acid salt is preferably a salt of a carboxylic acid having from 6 to 30 to carbon atoms, more preferably a salt of a carboxylic acid having from 8 to 25 carbon atoms, and even more preferably a salt of a carboxylic acid having from 10 to 20 carbon atoms. The carboxylic acid salt may be a monocarboxylic acid salt or a polycarboxylic acid salt.

Examples of monocarboxylic acid salts include caprylic acid salts such as potassium caprylate, sodium caprylate and zinc caprylate; octanoic acid salts such as potassium octanoate, sodium octanoate and zinc octanoate; pelargonic acid salts such as potassium pelargonate and sodium pelargonate; capric acid salts such as potassium caprate and sodium caprate; undecylenic acid salts such as potassium undecylenate and sodium undecylenate; lauric acid salts such as potassium laurate, sodium laurate, calcium laurate, barium laurate and zinc laurate; myristic acid salts such as potassium myristate, sodium myristate, zinc myristate and magnesium myristate; pentadecanoic acid salts such as potassium pentadecanoate and sodium pentadecanoate; palmitic acid salts such as potassium palmitate, sodium palmitate and calcium palmitate; margaric acid salts such as potassium margarate and sodium margarate; stearic acid salts such as lithium stearate, sodium stearate, magnesium stearate, calcium stearate, barium stearate, zinc stearate and aluminum stearate; isostearic acid salts such as potassium isostearate and sodium isostearate; oleic acid salts such as potassium oleate and sodium oleate; ricinolic acid salts such as calcium ricinolate, barium ricinolate and zinc ricinolate; linoleic acid salts such as potassium linoleate, sodium linoleate and calcium linoleate; linolenic acid salts such as potassium linolenate and sodium linolenate; arachidonic acid salts such as potassium arachidonate and sodium arachidonate; behenic acid salts such as potassium behenate, sodium behenate and calcium behenate; docosahexaenoic acid salts such as sodium docosahexanoate; coconut acid salts such as potassium cocoate and sodium cocoate; palm oil fatty acid salts such as the calcium salt of palm oil fatty acids; and isopropyltitanium triisostearate. Of these, stearic acid salts and myristic acid salts are preferred.

Examples of polycarboxylic acid salts include octanedioic acid salts such as disodium octanedioate and dipotassium octanedioate; nonanedioic acid salts such as disodium nonanedioate and dipotassium nonanedioate; decanedioic acid salts such as disodium decanedioate and dipotassium decanedioate; undecanedioic acid salts such as disodium undecanedioate and dipotassium undecanedioate; dodecanedioic acid salts such as disodium dodecanedioate and dipotassium dodecanedioate; tridecanedioic acid salts such as disodium tridecanedioate and dipotassium tridecanedioate; tetradecanedioic acid salts such as disodium tetradecanedioate and dipotassium tetradecanedioate; pentadecanedioic acid salts such as disodium pentadecanedioate and dipotassium pentadecanedioate; hexadecanedioic acid salts such as disodium hexadecanedioate and dipotassium hexadecanedioate; heptadecanedioic acid salts such as disodium heptadecanedioate and dipotassium heptadecanedioate; octadecanedioic acid salts such as disodium octadecanedioate and dipotassium octadecanedioate; nonadecanedioic acid salts such as disodium nonadecanedioate and dipotassium nonadecanedioate; and eicosanedioic acid salts such as disodium eicosanedioate and dipotassium eicosanedioate. Isomers of these having a branched structure, and salts of polycarboxylic acids with a functionality of three or more may also be used.

The amino acids and derivatives thereof are preferably ones having from 6 to 30 carbon atoms, and more preferably ones having from 10 to 25 carbon atoms. Examples of such amino acids include the following amino acids and amino acid derivatives: sarcosine derivatives such as lauroyl sarcosine, myristoyl sarcosine, palmitoyl sarcosine and cocoyl sarcosine; glutamic acid derivatives such as lauroyl glutamic acid, myristoyl glutamic acid, palmitoyl glutamic acid, stearoyl glutamic acid, coconut oil fatty acid acylglutamic acid, cocoyl glutamic acid, acylglutamic acid and dilauroyl glutamic acid; glycine derivatives such as lauroyl glycine, myristoyl glycine, palmitoyl glycine, palmitoyl methylglycine, coconut oil fatty acid acyl glycine and cocoyl glycine; alanine derivatives such as lauroyl methylalanine, myristoyl methylalanine, cocoyl alanine and cocoyl methylalanine; lysine derivatives such as lauroyl lysine, myristoyl lysine, palmitoyl lysine, stearoyl lysine, oleoyl lysine and acylated lysine; aspartic acid derivatives such as lauroyl aspartic acid, myristoyl aspartic acid, palmitoyl aspartic acid and stearoyl aspartic acid; taurine derivatives such as lauroyl taurine, lauroyl methyltaurine, myristoyl taurine, myristoyl methyltaurine, palmitoyl taurine, palmitoyl methyl taurine, stearoyl taurine and stearoyl methyltaurine; and proline derivatives such as lauroyl proline, myristoyl proline and palmitoyl proline.

The salts of amino acids and amino acid derivatives are preferably salts of amino acids and amino acid derivatives having from 6 to 30 carbon atoms, and more preferably salts of amino acids and amino acid derivatives having from 10 to 25 carbon atoms. Examples of such salts include the following: sarcosine salts such as potassium lauroyl sarcosinate, sodium lauroyl sarcosinate, potassium myristoyl sarcosinate, sodium myristoyl sarcosinate, potassium palmitoyl sarcosinate, sodium palmitoyl sarcosinate, potassium cocoyl sarcosinate and sodium cocoyl sarcosinate; glutamic acid salts such as potassium lauroyl glutamate, sodium lauroyl glutamate, potassium myristoyl glutamate, sodium myristoyl glutamate, sodium palmitoyl glutamate, magnesium palmitoyl glutamate, potassium stearoyl glutamate, sodium stearoyl glutamate, potassium coconut oil fatty acid acylglutamate, sodium coconut oil fatty acid acylglutamate, potassium cocoyl glutamate, sodium cocoyl glutamate, potassium acylglutamate, sodium acylglutamate, sodium dilauroyl glutamate lysine and sodium polyglutamate; glycine salts such as potassium lauroyl glycine, sodium lauroyl glycine, potassium myristoyl glycine, sodium myristoyl glycine, sodium palmitoyl glycine, sodium palmitoyl methylglycine, potassium coconut oil fatty acid acylglycine, sodium coconut oil fatty acid acylglycine, potassium cocoyl glycine and sodium cocoyl glycine; alanine salts such as potassium lauroyl methylalanine, sodium lauroyl methylalanine, sodium myristoyl methylalanine, sodium cocoyl alanine and sodium coconut oil fatty acid methylalanine; aspartic acid salts such as potassium lauroyl aspartate, sodium lauroyl aspartate, potassium myristoyl aspartate, sodium myristoyl aspartate, potassium palmitoyl aspartate, sodium palmitoyl aspartate, potassium stearoyl aspartate and sodium stearoyl aspartate; lauroyl taurine salts such as sodium lauroyl taurate and calcium lauroyl taurate; taurine salts such as sodium lauroyl taurate, calcium lauroyl taurate, sodium lauroyl methyltaurate, potassium myristoyl taurate, sodium myristoyl taurate, sodium myristoyl methyltaurate, potassium palmitoyl taurate, sodium palmitoyl taurate, potassium palmitoyl methyltaurate, sodium palmitoyl methyltaurate, potassium stearoyl taurate, sodium stearoyl taurate and sodium stearoyl methyltaurate; and proline salts such as sodium lauroyl proline, sodium myristoyl proline and sodium palmitoyl proline.

The organosilicon compounds are exemplified by alkylated silanes having at least one alkyl group of from 6 to 30 carbon atoms, alkylated silazanes having at least one alkyl group of from 6 to 30 carbon atoms, trialkoxysilanes having at least one alkoxy group of from 6 to 30 carbon atoms, octyltrialkoxysilanes, triethoxycaprylylsilane and 3-meth-acryloxypropyltrimethoxysilane.

The silicone compounds are exemplified by methylhy-drogenpolysiloxane, methylpolysiloxane (methicone), dim-ethylpolysiloxane (dimethicone), triethoxysilylethyl polydi-methylsiloxyethyl dimethicone, methylphenylpolysiloxane, triethoxysilylethyl polydimethylsiloxyethyl hexyl dimethi-cone, cyclic silicones, crosslinked silicones, acrylic-silicone graft polymers, organic silicone resin partially crosslinked-type organopolysiloxane polymers, tetramethyltetrahydro-gencyclotetrasiloxane, trimethylsiloxysilicic acid, amino-modified silicones, carboxylic acid-modified silicones, fluorinated silicones, silicone gums, acrylic silicones, sili-cone resins, triethoxysilylethyl polydimethylsiloxyethyl dimethicone, triethoxysilylethyl polydimethylsiloxyethyl hexyl dimethicone and fluorinated silicones.

Examples of the fluorine compounds include perfluoro-alkylphosphate esters, perfluoroalkylsilanes, perfluoroalky-lalkoxysilanes, perfluoroalkyl group-containing esters, salts of perfluoroalkylphosphate salts, perfluoropolyethers, fluo-rosilicones, fluorinated silicone resins, trimethoxy(3,3,3-trifluoropropyl)silane and tridecafluorooctylfriethoxysilane.

The sulfate esters are exemplified by alkyl sulfate esters and salts thereof, polyoxyethylene aryl ether sulfate esters and salts thereof, polyoxyethylene alkyl ether sulfate esters and salts thereof, salts of polyoxyalkylene alkyl ether sulfate esters, polyoxyalkylene alkenyl ether sulfuric acid salts, and polyoxyethylene castor oil ether sulfate esters and salts thereof.

The alkyl sulfate esters and salts thereof are exemplified by ones having an alkyl group of from 6 to 30 carbon atoms. Specific examples include lauryl sulfuric acid, potassium lauryl sulfate, sodium lauryl sulfate, ammonium lauryl sul-fate, myristyl sulfuric acid, potassium myristyl sulfate, sodium myristyl sulfate, ammonium myristyl sulfate, cetyl sulfuric acid, sodium cetyl sulfate, ammonium cetyl sulfate, stearyl sulfuric acid, sodium stearyl sulfate, ammonium stearyl sulfate, oleyl sulfuric acid, sodium oleyl sulfate and ammonium oleyl sulfate.

The polyoxyethylene aryl ether sulfate esters and salts thereof are preferably ones having a hydrophilic-lipophilic balance (HLB) of 6 or less, examples of which include polyoxyethylene polycyclic phenyl ether sulfate ester and salts of polyoxyethylene polycyclic phenyl ether sulfate ester, such as sodium polyoxyethylene polycyclic phenyl ether sulfate and ammonium polyoxyethylene polycyclic phenyl ether sulfate; and also polyoxyethylene aryl ether sulfate esters and sodium polyoxyethylene aryl ether sul-fates.

The polyoxyethylene alkyl ether sulfate esters and salts thereof are preferably ones having a HLB of 6 or less, examples of which include polyoxyethylene alkyl ether sulfate esters, sodium polyoxyethylene lauryl ether sulfate, ammonium polyoxyethylene lauryl ether sulfate, sodium polyoxyethylene myristyl ether sulfate, ammonium poly-oxyethylene myristyl ether sulfate, sodium polyoxyethylene cetyl ether sulfate, ammonium polyoxyethylene cetyl ether sulfate, sodium polyoxyethylene stearyl ether sulfate, ammonium polyoxyethylene stearyl ether sulfate, sodium polyoxyethylene oleyl ether sulfate and ammonium poly-oxyethylene oleyl ether sulfate.

The polyoxyalkylene alkyl ether sulfate ester salts are preferably ones having a HLB of 6 or less, examples of which include sulfate ester sodium salts of polyoxyethylene-polyoxypropylene block copolymers, sulfate ester sodium salts of polyoxyethylene-polyoxybutylene block copoly-mers and sulfate ester sodium salts of alkyl ethers of polyoxyethylene-polyoxypropylene block copolymers. The polyoxyalkylene alkenyl ether sulfates are preferably ones having a HLB of 6 or less, examples of which include sulfate ester ammonium salts of alkenyl ethers of polyoxyethylene-polyoxyalkylene block copolymers. The polyoxyethylene castor oil ether sulfate esters and salts thereof are preferably ones having a HLB of 6 or less, examples of which include polyoxyethylene castor oil ether sulfate esters and ammo-nium polyoxyethylene castor oil ether sulfate.

The sulfonic acids and salts thereof are preferably ones having from 6 to 30 carbon atoms, examples of which include alkyl sulfonic acids and salts thereof, such as lauryl sulfonic acid, sodium lauryl sulfonate, ammonium lauryl sulfonate, myristyl sulfonic acid, sodium myristyl sulfonate, ammonium myristyl sulfonate, cetyl sulfonic acid, sodium cetyl sulfonate, ammonium cetyl sulfonate, stearyl sulfonic acid, sodium stearyl sulfonate, to ammonium stearyl sulfonate, oleyl sulfonic acid, sodium oleyl sulfonate and ammonium oleyl sulfonate; dodecylbenzene sulfonic acid and salts thereof, such as dodecylbenzene sulfonic acid, ammonium dodecylbenzene sulfonate, sodium dodecylben-zene sulfonate and calcium dodecylbenzene sulfonate; alkylene disulfonic acids and salts thereof, such as alkylene disulfonic acids and sodium alkylene disulfonic acids; dial-kyl succinate sulfonic acids and salts thereof, such as dialkyl succinate sulfonic acid and sodium dialkyl succinate sulfonate; monoalkyl succinate sulfonic acids and salts thereof, such as monoalkyl succinate sulfonic acids and disodium monoalkyl succinate sulfonates; naphthalene sulfonic acid formalin condensates and salts thereof, such as naphthalene sulfonic acid formalin condensates and sodium salts of naphthalene sulfonic acid formalin condensates; olefin sulfonic acid salts such as sodium olefin sulfonates and ammonium olefin sulfonates; isethionic acids such as lauroyl isethionic acid, myristoyl isethionic acid, palmitoyl isethionic acid and, stearoyl isethionic acid; isethionic acid salts such as potassium lauroyl isethionate, sodium lauroyl isethionate, sodium myristoyl isethionate, sodium palmitoyl isethionate and sodium stearoyl isethionate; and sulfosuc-cinic acids and salts thereof, such as sodium dihexyl sulfo-succinate, sodium dioctyl sulfosuccinate, ammonium dioctyl sulfosuccinate, sodium didecyl sulfosuccinate and sodium diisobutyl sulfosuccinate.

The phosphate esters and salts thereof are exemplified by polyoxyalkylene alkyl ether phosphate esters and alkyl phosphate esters and salts thereof. The polyoxyalkylene alkyl ether phosphate esters are preferably ones having a HLB value of 6 or below, examples of which include polyoxyethylene (2) stearyl ether phosphate esters.

The alkyl phosphate esters and salts thereof are exempli-fied by ones having an alkyl group of from 6 to 30 carbon atoms, including the following: octyl phosphoric acid and salts thereof, such as octyl phosphoric acid and potassium octyl phosphate; nonyl phosphoric acid and salts thereof, such as nonyl phosphoric acid and potassium nonyl phos-phate; decyl phosphoric acid and salts thereof, such as decyl phosphoric acid and potassium decyl phosphate; undecyl phosphoric acid and salts thereof, such as undecyl phos-phoric acid and potassium undecyl phosphate; lauryl phos-phoric acid and salts thereof, such as lauryl phosphoric acid and potassium lauryl phosphate; myristyl phosphoric acid and salts thereof, such as myristyl phosphoric acid and potassium myristyl phosphate; cetyl phosphoric acid and salts thereof, such as cetyl phosphoric acid, potassium cetyl phosphate, sodium cetyl phosphate, calcium cetyl phosphate and zinc cetyl phosphate; and stearyl phosphoric acid and salts thereof, such as stearyl phosphoric acid and potassium stearyl phosphate.

The lactic acid esters and salts thereof are exemplified by ones having from 6 to 30 carbon atoms, including lauryl lactate, myristyl lactate, cetyl lactate, oleyl lactate, octyldodecyl lactate, sodium stearoyl lactate, calcium stearoyl lactate, sodium isostearyl lactate and sodium lauroyl lactate.

Aside from the above-mentioned compounds, oils, acrylic compounds, acrylic resins, titanium coupling agents, inorganic compounds, metal oxides and solid lubricants that are used as additives in cosmetics may be used, in addition to which known surfactants and the like may be used as hydrophobizing agents.

Examples of the oils include petrolatum, liquid paraffins, squalane, paraffin wax, linseed oil, cottonseed oil, coconut oil, castor oil, egg oil, lanolin fatty acids, propylene glycol dicaprate, glyceryl trioctanoate, cetyl 2-ethylhexanoate, isocetyl stearate, stearyl alcohol, cetyl alcohol, oleyl alcohol, beef tallow, beeswax, spermaceti, Japan wax, lanolin, carnauba wax and candelilla wax.

Examples of the acrylic compounds include alkyl (meth) acrylates. Examples of the acrylic resins include copolymers of (meth)acrylic acid and styrene compounds, as well as salts thereof; copolymers of (meth)acrylic acid and (meth) acrylate ester compounds, as well as salts thereof; copolymers of (meth)acrylic acid and vinyl ester compounds, as well as salts thereof; copolymers of (meth)acrylic acid and olefin compounds, as well as salts thereof; and copolymers of (meth)acrylic acid and conjugated diene compounds, as well as salts thereof.

Examples of the titanium coupling agents include alkyl titanates, pyrophosphoric acid titanates, phosphonic acid titanates and amino acid titanates.

An example of the inorganic compounds is alumina. An example of the metal oxides is titanium oxide.

Examples of the solid lubricants include polyolefin waxes (e.g., polyethylene wax), paraffin waxes (e.g., synthetic paraffins, natural paraffins), fluoropolymer waxes (e.g., polytetrafluoroethylene), fatty amide compounds (e.g., stearamide, palmitamide), metal sulfides (e.g., molybdenum disulfide, tungsten disulfide), graphite, graphite fluoride, boron nitride, polyalkylene glycols and alkali metal sulfates.

Of these, from the standpoint of production, carboxylic acids and salts thereof, amino acids and salts thereof and organosilicon compounds are preferred as the hydrophobizing agent; from an environmental standpoint, carboxylic acids and salts thereof and amino acids and salts thereof are more preferred. The carboxylic acids and salts thereof and the amino acids and salts thereof have low molecular weights and are easily decomposed by microorganisms in the environment.

From an environmental standpoint and the standpoint of production, carboxylic acid salts, amino acid salts and salts of amino acid derivatives are more preferred as the hydrophobizing agent. Of these, from an environmental standpoint, salts having organic ions or metallic ions as the cations are preferred. An example of an organic ion is the ammonium ion. Examples of the metallic ions include various metallic ions such as lithium, potassium, calcium, sodium, magnesium, aluminum, zinc, iron, nickel, tin, lead, copper, cobalt, manganese, strontium, barium, cadmium, mercury, silver, platinum and gold ions. Of these, from the standpoints of the environment, biological safety, versatility and cost, calcium, sodium, magnesium, potassium and ammonium ions are preferred. Monovalent metallic ions that readily make carboxylic acid salts and amino acid salts hydrophilic are especially preferred, with potassium and sodium ions being specifically preferred. The sodium ion, which is a versatile metallic ion, is excellent as well from the standpoint of the subsequently described considerations.

Hydrophobization is described in detail later in the Specification.

The hydrophobic alginic acid particles of the invention have an average particle size which is preferably 5 mm or less, and more preferably, in order of increasing preference: 1 mm or less, 500 μm or less, 100 μm or less, 60 μm or less, 30 μm or less, 15 μm or less, or 10 μm or less. The lower limit is preferably at least 0.1 pin, more preferably at least 0.5 μm, and even more preferably at least 1.0 μm. In this invention, the average particle size refers to the volume mean particle diameter (MV) obtained by the laser diffraction scattering method.

The hydrophobic alginic acid particles of the invention have shapes which, although not particularly limited, may be physically or chemically shape-controlled or physically pulverized shapes, such as spherical, approximately spherical, flattened or recessed shapes. From the standpoint of the feel, slip characteristics and control of the particle size distribution, particles that are physically or chemically shape-controlled, such as spherical, approximately spherical, flattened or recessed particles, are preferred. Particles with irregular shapes that are formed of curves without sharp edges, such as approximately spherical, flattened and recessed shapes, have good optical properties and therefore are more preferred.

The hydrophobic alginic acid particles of the invention have a water absorption per 100 g of particles ($A_w$, mL/100 g) and an oil absorption per 100 g of particles ($A_o$, mL/100 g) such that the water absorption is lower than the oil absorption (($A_w/A_o$)<1). By satisfying this relationship, the particles, while exhibiting hydrophobic effects during use, maintain a non-dissolving state in water but gradually dissolve in seawater (salt water) and are readily decomposed by microorganisms. To readily achieve this effect, $A_w$ and $A_o$ more preferably satisfy the condition $A_w/A_o \le 0.75$, even more preferably satisfy the condition $A_w/A_o \le 0.65$, and most preferably satisfy the condition $A_w/A_o \le 0.5$.

Water absorption by the hydrophobic alginic acid particles of the invention is preferably 80 mL/100 g or less, more preferably 60 mL/100 g or less, even more preferably 50 mL/100 g or less, and most preferably 40 mL/100 g or less. At a water absorption of 80 mL/100 g or less, the particles can be used in the same way as and are by no means inferior to existing general-purpose polymer particles made of acrylic or nylon. To readily achieve this effect, the lower limit in the water absorption is preferably at least 1 mL/100 g, more preferably at least 5 mL/100 g, and even more preferably at least 10 mL/100 g.

Oil absorption by the hydrophobic alginic acid particles of the invention is preferably at least 35 mL/100 g, more preferably at least 50 mL/100 g, and even more preferably at least 65 mL/100 g or less. At an oil absorption of at least 35 mL/100 g, in cosmetic applications, the improved affinity with oils results in a higher dispersibility and also better stability in an emulsion or cream. To readily achieve these effects, the upper limit in the oil absorption is preferably not more than a 200 mL/100 g, more preferably not more than 150 mL/100, and even more preferably not more than 120 mL/100 g.

The water absorption and oil absorption can be modified by adjusting the type, amount of pickup, etc. of the subsequently described hydrophobizing agent. In this invention, the oil absorption is a value measured in general accordance with the boiled linseed oil method described in JIS K 5101. The water absorption is a value obtained as follows. One gram of the particles is placed in a 500 mL beaker, following which 200 mL of deionized water is added and stirring is carried out for 30 minutes. The beaker contents are then transferred to a 500 mL centrifuge tube and centrifugation is carried out using a centrifuge. Following centrifugation, the supernatant is gently discarded, the sample is removed from the centrifuge tube and the weight ($W_w$) is measured. The sample is then dried to a constant weight in a 105° C. drying oven and the dry weight ($D_w$) is measured. The water absorption is calculated from the following formula.

$$\text{Water absorption (mL/100 g)} = ((W_w - D_w)/D_w) \times 100$$

The hydrophobic alginic acid particles of the invention have a contact angle when a droplet of water is dropped onto the particles that is preferably at least 30°, and more preferably, in order of increasing preference: 50° or more, 60° or more, 80° or more, 90° or more, and 100° or more. The contact angle has an upper limit which is not particularly limited, but the practical value for which is 170° or less, and more preferably, in order of increasing preference: 160° or less, 150° or less, and 140° or less. At a contact angle in this range, the hydrophobic effects and the solubility and degradability of the particles in the environment are fully exhibited.

The hydrophobic alginic acid particles of the invention are such that, letting SD1, SD2 and SD3 be the respective percent transmittances to 560 nm wavelength light of a dispersion prepared by dispersing the hydrophobic alginic acid particles in a 3 wt % aqueous solution of sodium chloride to a concentration of 0.1 wt % when 72 hours, 240 hours and 720 hours have elapsed following preparation, and letting WD1, WD2 and WD3 be the respective percent transmittances to 560 nm wavelength light of a dispersion prepared by dispersing the hydrophobic alginic acid particles in water to a concentration of 0.1 wt % when 72 hours, 240 hours and 720 hours have elapsed following preparation, at least one of the ratios WD1/SD1, WD2/SD2 and WD3/SD3 is preferably 0.9 or less, more preferably 0.8 or less, and even more preferably 0.5 or less. At 0.9 or less, the shapes of the alginic acid particles change and an increase in clarity as the particles dissolve can be confirmed. The lower limit for WD1/SD1, WD2/SD2 and WD3/SD3, although not particularly limited, is generally about 0.1.

In cases where a dissolution effect cannot be confirmed after about 720 hours, due to concerns over environmental pollution in the oceans (marine pollution), the adsorption of chemical substances and adverse effects on the ecosystem, long-term particle shape retention in excess of this is sometimes undesirable. Hence, from the standpoint of the environmental impact, it is preferable for WD3/SD3≤0.9, more preferable for WD2/SD2≤0.9, and still more preferable for WD1/SD1≤0.9.

Prior to hydrophobization, calcium alginate by itself has a good affinity to water. Accordingly, when placed in an aqueous solution of sodium chloride under the above conditions, there is a tendency for sodium substitution to occur and for the calcium alginate to rapidly dissolve. In other words, the fact that it readily dissolves also is a practical problem, and thus limits applications. Hence, it is desirable for the particles to maintain shape stability for about 0.05 hour, preferably about 0.1 hour, and especially about 0.25 hour. That is, letting $SD^x$ be the percent transmittance to 560 mu wavelength light of a dispersion prepared by dispersing the hydrophobic alginic acid particles in a 3 wt % aqueous solution of sodium chloride to a concentration of 0.1 wt % when x hours have elapsed following preparation, and letting $WD^x$ be the percent transmittance to 560 nm wavelength light of a dispersion prepared by dispersing the hydrophobic alginic acid particles in water to a concentration of 0.1 wt % when x hours have elapsed following preparation, it is preferable for at least one of the ratios $WD^{0.05}/SD^{0.05}$, $WD^{0.1}/SD^{0.1}$ and $WD^{0.25}/SD^{0.25}$ to be larger than 0.9. Hydrophobic calcium alginate particles according to the invention, owing to the fact that the stability of the calcium alginate is retained and dissolution can be retarded due to hydrophobization, are able to maintain a quality consistent with practical utility.

[Methods of Producing Hydrophobic Alginic Acid Particles]

Examples of methods for producing the hydrophobic alginic acid particles of the invention include the following.

(1) A method which includes the step of hydrophobizing alginic acid particles containing a polyvalent metal salt of alginic acid (Method 1).

(2) A method which includes the steps of spray-drying a solution containing a monovalent salt of alginic acid and a hydrophobizing agent to obtain particles, and then crosslinking the particles using a polyvalent metal salt and at the same time hydrophobizing the particles (Method 2).

(3) A method which includes the steps of forming a water-in-oil emulsion which contains a monovalent salt of alginic acid and a hydrophobizing agent in the water droplets, and then carrying out crosslinking treatment using a polyvalent metal salt and at the same time carrying out hydrophobization (Method 3).

Method 1 includes the step of hydrophobizing alginic acid particles containing a polyvalent metal salt of alginic acid. The alginic acid particles can be produced by a known method. For example, as described in JP-A H05-222208, the particles can be produced by spray-drying a solution of a dissolved monovalent salt of alginic acid to form particles, and then carrying out crosslinking treatment using a polyvalent metal salt. The monovalent salt of alginic acid and the polyvalent metal salt are subsequently described.

The alginic acid particles can be produced by forming a water droplet-in-oil (W/O) emulsion that contains a monovalent salt of alginic acid in water, and then subjecting the emulsion to crosslinking treatment using a polyvalent metal salt. An example of a method for forming the W/O emulsion involves first preparing a solution (Solution A) of a monovalent salt of alginic acid dissolved in water or a mixed solvent of water and a hydrophilic organic solvent. If necessary, heating may be carried out at this time. Next, Solution A and a hydrophobic organic solvent are mixed together, and then emulsified using an agitator, homogenizer or the like. At the time of mixture, Solution A may be added to the hydrophobic organic solvent, or the hydrophobic organic solvent may be added to Solution A.

To control the particle size of the water droplets in the W/O emulsion, a Solution B of a surfactant or a polymer stabilizer dissolved in the hydrophobic organic solvent may be used at this time in place of the hydrophobic organic solvent. In this case, Solution A and Solution B are mixed together, and then emulsified using an agitator, homogenizer or the like. At the time of mixture, Solution A may be added to Solution B, or Solution B may be added to Solution A.

Another example of a method of forming the W/O emulsion is to charge a container all at once with the monovalent salt of alginic acid, water, surfactant, hydrophobic organic solvent and other necessary ingredients, and then carry out emulsification using an agitator, homogenizer or the like.

Crosslinking treatment can be carried out by adding a polyvalent metal salt-containing solution to the W/O emulsion and stirring. Alternatively, it can be carried out by adding the W/O emulsion to a polyvalent metal salt-containing solution and stirring. Use may be made of the same polyvalent metal salt-containing solution as that described subsequently in the explanation of Method 2.

If necessary, crosslinking treatment may be carried out under heating. Heating may be carried out when adding the polyvalent metal salt-containing solution to the dispersion, may be carried out during stirring following such addition, or may be carried out at both of these times. The heating temperature is preferably between 10° C. and 100° C., and more preferably between 15° C. and 80° C. The treatment time is preferably from 0.5 to 24 hours, and more preferably from 1 to 12 hours.

After crosslinking treatment, if necessary, washing and drying of the particles may be carried out to give the alginic acid particles. Washing may be carried out by an ordinary method, such as that of removing the solvent following crosslinking treatment, adding water and centrifuging. Drying may be carried out by an ordinary method such as spray drying, vacuum drying or freeze drying.

It is also possible to use a commercial product as the alginic acid particles. Examples include Fravikafine® (from Nisshiubo Chemical Inc.) and the calcium alginate CA series from Kimika Corporation.

The method of hydrophobizing the alginic acid particles is exemplified by a method in which the hydrophobizing agent is dissolved in a solvent, following which the alginic acid particles are placed in the solution and dispersed, thereby causing the hydrophobizing agent to deposit on the surface of the particles or both on the surface and at the interior of the particles. At this time, where necessary, deposition can be efficiently carried out by heating or concentration. In cases where heating is carried out, the temperature is preferably between 10° C. and 100° C., and more preferably between 30° C. and 80° C. Concentration may be carried out by, for example, heating the reaction system and removing the solvent that evaporates. The hydrophobizing treatment time is preferably from 0.5 to 24 hours, and more preferably from 1 to 12 hours.

The solvent may be suitably selected from among those solvents which are able to disperse the alginic acid particles and can dissolve the hydrophobizing agent that is be used. Illustrative examples include water; alcohols such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 1-hexanol, 2-methyl-1-pentanol, 4-methyl-2-pentanol, 2-ethylbutanol, 1-heptanol, 2-heptanol, 3-heptanol, 2-octanol, 2-ethyl-1-hexanol, benzyl alcohol and cyclohexanol; ether alcohols such as methyl cellosolve, ethyl cellosolve, isopropyl cellosolve, butyl cellosolve and diethylene glycol monobutyl ether; ketones such as acetone, methyl ethyl ketone, methyl isobutyl ketone and cyclohexanone; esters such as ethyl acetate, butyl acetate, ethyl propionate and cellosolve acetate; aliphatic or aromatic hydrocarbons such as pentane, 2-methylbutane, n-hexane, cyclohexane, 2-methylpentane, 2,2-dimethylbutane, 2,3-dimethylbutane, heptane, n-octane, isooctane, 2,2,3-trimethylpentane, decane, nonane, cyclopentane, methylcyclopentane, methylcyclohexane, ethylcyclohexane, p-menthane, dicyclohexyl, benzene, toluene, xylene and ethylbenzene; halogenated hydrocarbons such as carbon tetrachloride, trichloroethylene, chlorobenzene and tetrabromoethane; ethers such as diethyl ether, dimethyl ether, trioxane and tetrahydrofuran; acetals such as methylal and diethylacetal; carboxylic acids such as formic acid, acetic acid and propionic acid; sulfur or nitrogen-containing organic compounds such as nitropropene, nitrobenzene, dimethylamine, monoethanolamine, pyridine, dimethylformamide, dimethylsulfoxide, N-methyl-2-pyrrolidone and acetonitrile; and ionic liquids. These solvents may be of one type used alone or two or more may be used in admixture.

The hydrophobizing agent used may be one that is mentioned above. When a carboxylic acid salt or amino acid salt in particular is used as the hydrophobizing agent, this gives rise to ion exchange with at least some of the ion-crosslinked polyvalent metal ions, accompanied by chemical bonding with the hydrophobizing agent. Monodisperse crosslinked particles of strengthened hydrophobicity can thus be obtained following treatment, which is desirable.

Hydrophobizing treatment is carried out such that the weight ratio between the alginic acid particles and the hydrophobizing agent in the solvent, expressed as "alginic acid particles:hydrophobizing agent" is preferably from 99.9:0.1 to 70:30, more preferably from 99.5:0.5 to 80:20, even more preferably from 99:1 to 85:15, and still more preferably from 98:2 to 90:10.

Following hydrophobization, if necessary, the particles are washed and dried, thereby obtaining hydrophobic alginic acid particles. Washing may be carried out by an ordinary to method, such as that of, for example, removing the solvent following hydrophobization, adding water and centrifuging. Drying may be carried out by an ordinary method such as spray drying, vacuum drying or freeze drying.

Method 2 includes the steps of spray-drying a solution containing a monovalent salt of alginic acid and a hydrophobizing agent to obtain particles, and then crosslinking the particles using a polyvalent metal salt and at the same time hydrophobizing the particles.

The monovalent salt of alginic acid may be an inorganic salt or an organic salt. Examples include sodium alginate, potassium alginate and ammonium alginate. The monovalent salt of alginic acid has a viscosity as a 1 wt % or 10 wt % aqueous solution that is preferably from 0.01 to 2,000 mPa·s, more preferably from 0.1 to 1,000 mPa·s, and most preferably from 1.0 to 500 mPa·s. Taking into consideration the productivity, it is more preferable for the viscosity of a 10 wt % aqueous solution to satisfy the above range. The viscosity is a value measured at 20° C. with a BL-type Brookfield viscometer.

The solvent used in the solution containing a monovalent salt of alginic acid and a hydrophobizing agent is preferably water or a mixed solvent of water with a hydrophilic organic solvent. The water may be, for example, tap water, deionized water or distilled water. Examples of hydrophilic organic solvents include methanol, ethanol, 1-propanol, 2-propanol, ethylene glycol, propylene glycol, butylene glycol, dipropylene glycol, methyl cellosolve, ethyl cellosolve, propyl cellosolve, diethylene glycol monobutyl ether, methyl cellosolve acetate, ethyl cellosolve acetate, methyl carbitol, ethyl carbitol, butyl carbitol, ethyl carbitol acetate, formic acid, acetic acid, propionic acid, acetone, tetrahydrofuran, dimethylformamide, dimethylsulfoxide, trioxane, tetrahydrofuran, N-methyl-2-pyrrolidone, dimethylamine, monoethanolamine, pyridine and acetonitrile. These may be of one type used alone or two or more may be used in admixture. Of these, water or a mixed solvent of water and a lower alcohol of 1 to 3 carbons is preferred.

If necessary, a hydrophobic organic solvent may also be added to the above solvent. Examples of the hydrophobic organic solvent include higher alcohols such as 1-butanol, 2-butanol, isobutyl alcohol, tert-butyl alcohol, 1-pentanol, 2-pentanol, 3-pentanol, to 2-methyl-1-butanol, isopentyl alcohol, tert-pentyl alcohol, 1-hexanol, 2-methyl-1-penta-nol, 4-methyl-2-pentanol, 2-ethylbutanol, 1-heptanol, 2-heptanol, 3-heptanol, 2-octanol, 2-ethyl-1-hexanol, benzyl alcohol and cyclohexanol; ether alcohols such as butyl cellosolve; ketones such as methyl ethyl ketone, methyl isobutyl ketone and cyclohexanone; esters such as ethyl acetate, butyl acetate, ethyl propionate and cellosolve acetate; aliphatic or aromatic hydrocarbons such as pentane, 2-methylbutane, n-hexane, cyclohexane, 2-methylpentane, 2,2-dimethylbutane, 2,3-dimethylbutane, heptane, n-octane, isooctane, 2,2,3-trimethylpentane, decane, nonane, cyclo-pentane, methylcyclopentane, methylcyclohexane, ethylcy-clohexane, p-menthane, dicyclohexyl, benzene, toluene, xylene and ethylbenzene; halogenated hydrocarbons such as carbon tetrachloride, trichloroethylene, chlorobenzene and tetrabromoethane; ethers such as diethyl ether and dimethyl ether; acetals such as methylal and diethyl acetal; the following cyclic, linear or branched silicone oils and copo-lymers thereof: dimethylpolysiloxanes such as hexam-ethykyclohisiloxane (D3), octamethylcyclotetrasiloxane (D4), decamethylcyclopentasiloxane (D5), dodecamethyl-cyclohexasiloxaue (D6), tetradecamethylcycloheptasiloxane (D7), hexamethyldisiloxane, octamethyltrisiloxane and decamethyltetrasiloxane, and also methyl trimethicone, methyl phenyl polysiloxane, diphenyl polysiloxane, diphe-nyl siloxyphenyl trimethicone, trimethyl siloxyphenyl dime-thicone, caprylyl methicone and cetyl dimethicone; and sulfur or nitrogen-containing organic compounds such as nitropropene and nitrobenzene.

In this invention, "hydrophilic organic solvent" refers to an organic solvent for which an equal volume mixture with water maintains a uniform appearance. Also, "hydrophobic organic solvent" refers to a solvent for which, after being gently mixed with the same volume of pure water at one atmosphere ($1.013 \times 10^5$ Pa) and a temperature of 20° C. and allowed to quiet down, the mixture is unable to maintain a uniform appearance.

The above-described hydrophobizing agents may be used as the hydrophobizing agent in Method 2, although it is essential to suitably select one that dissolves in the above solvent. For example, when water is used as the solvent, it is preferable to use a carboxylic acid salt or an amino acid salt that dissolves in water. Even one that dissolves in the solvent by heating may be used as the hydrophobizing agent.

The mixing ratio of the monovalent salt of alginic acid and the hydrophobizing agent in the solution, expressed as "monovalent salt of alginic acid:hydrophobizing agent," is preferably from 99.9:0.1 to 70:30, more preferably from 99.5:0.5 to 80:20, even more preferably from 99:1 to 85:15, and still more preferably from 98:2 to 90:10. At a mixing ratio in this range, sufficient hydrophobicity can be obtained and there is no danger of a drop in the degree of crosslinking.

The solids (monovalent salt of alginic acid and hydro-phobizing agent) concentration in the solution is preferably from 1 to 80 wt %, and more preferably from 5 to 50 wt %.

Spray drying may be carried out by a known method. For example, spray drying may be carried out by atomizing the solution in heated air using, for example, an ordinary rotary disk, two-fluid nozzle, jet flow or other type of spray dryer. Spray drying may be carried out at a disk rotational speed of from about 1,000 to about 40,000 rpm. The temperature of the hot air is the temperature required for moisture to evaporate, this being preferably between 60° C. and 250° C. Also, the solution may be sprayed into hot air while being heated.

Next, the particles obtained by spray drying (also referred to below as the "pre-crosslinking particles") are crosslinked using a polyvalent metal salt. Crosslinking treatment can be carried out by, for example, dispersing the pre-crosslinking particles in a medium, adding a polyvalent metal salt-containing solution to the dispersion, and stirring. Or the dispersion may be added to a polyvalent metal salt-contain-ing solution, and stirring then carried out.

The pre-crosslinking particles are dispersed in a medium to a concentration of preferably from 1 to 80 wt %, and more preferably from 30 to 60 wt %. The medium that disperses the particles is preferably a lower alcohol such as methanol, ethanol, 1-propanol or 2-propanol; an ether alcohol such as methyl cellosolve, ethyl cellosolve, isopropyl cellosolve, butyl cellosolve or diethylene glycol monobutyl ether; or a hydrophilic organic solvent such as acetone, tetrahydro-furan, dimethylformamide, N-methyl-2-pyrrolidone or acetonitrile. A single solvent such as a lower alcohol or a lower alcohol-containing mixed solvent is especially pre-ferred.

Examples of the polyvalent metal salt include calcium salts, strontium salts, magnesium salts, barium salts, radium salts, lead salts, zinc salts, nickel salts, iron salts, copper salts, cadmium salts, cobalt salts and manganese salts. From the standpoint of environmental considerations, safety and versatility, calcium salts are preferred. Specific examples of such polyvalent metal salts include calcium chloride, cal-cium sulfate, calcium carbonate, calcium hydroxide and calcium oxide. Calcium chloride is preferred in terms of solubility in water, handleability, costs and the like.

The concentration of the polyvalent metal salt in the polyvalent metal salt-containing solution is preferably from 1 to 40 wt %, and more preferably from 10 to 30 wt %. The solvent in the solution is preferably water; a lower alcohol solvent such as methanol, ethanol, 1-propanol or 2-propanol; or a mixed solvent of these. So long as the salt can be dissolved to the target concentration within a range that does not dissolve the particles, mixed solvents with other organic solvents are also acceptable.

Where necessary, crosslinking treatment may be carried out while heating. Heating may be carried out when the polyvalent metal salt-containing solution is added to the dispersion, may be carried out during stirring following addition, or may be carried out at both of these times. The temperature at this time is preferably between 10° C. and 100° C., and more preferably between 20° C. and 80° C. The treatment time is preferably from 0.5 to 24 hours, and more preferably from 1 to 12 hours. By heating, the solubility of the hydrophobizing agent can be increased; in addition, the viscosity of the medium decreases, and so the hydrophobi-zing agent more readily penetrates to the interior of the particles.

Because a monovalent salt of alginic acid and a hydro-phobizing agent are included in the pre-crosslinking par-ticles, by carrying out crosslinking treatment, hydrophobi-zation is also carried out at the same time.

After crosslinking treatment, if necessary, washing and drying of the particles may to be carried out to obtain the hydrophobic alginic acid particles. Washing may be carried out by an ordinary method such as that of, for example, removing the solvent following hydrophobization, adding water and centrifuging. Drying may be carried out by an ordinary method such as spray drying, vacuum drying or freeze drying.

Method 3 includes the steps of forming a W/O emulsion which contains a monovalent salt of alginic acid and a hydrophobizing agent in the water droplets, and then carry-ing out crosslinking treatment using a polyvalent metal salt and at the same time carrying out hydrophobization. The monovalent salt of alginic acid is exemplified by the same compounds as mentioned above in the explanation of Method 2. Also, it is essential for the hydrophobizing agent to be one which is present in the aqueous phase when the W/O emulsion is formed. Use of the above-mentioned carboxylic acid salts or amino acid salts is preferred.

An example of a method of forming a W/O emulsion is described. First, Solution A composed of a monovalent salt of alginic acid and a hydrophobizing agent dissolved in water or a mixed solvent of water and a hydrophilic organic solvent is prepared. If necessary, heating may be carried out at this time in order to dissolve the hydrophobizing agent. Next, Solution A and a hydrophobic organic solvent are mixed together and are emulsified using an agitator, homogenizer or the like. At the time of mixture, Solution A may be added to the hydrophobic organic solvent, or the hydrophobic organic solvent may be added to Solution A.

To control the particle size of the water droplets in the W/O emulsion, a Solution B of a surfactant or a polymer stabilizer dissolved in the hydrophobic organic solvent may be used at this time instead of the hydrophobic organic solvent. In this case, Solution A and Solution B are mixed together, and then emulsified using an agitator, homogenizer or the like. At the time of mixture, Solution A may be added to Solution B, or Solution B may be added to Solution A.

Another example of a method of forming the W/O emulsion is to charge a container all at once with the monovalent salt of alginic acid, hydrophobizing agent, water, surfactant, hydrophobic organic solvent and other necessary ingredients, and then carry out emulsification using an agitator, homogenizer or the like.

The mixing ratio of the monovalent salt of alginic acid and the hydrophobizing agent, expressed as "monovalent salt of alginic acid:hydrophobizing agent," is preferably from 99.9:0.1 to 70:30, more preferably from 99.5:0.5 to 80:20, even more preferably from 99:1 to 85:15, and still more preferably form 98:2 to 90:10. At a mixing ratio in this range, sufficient hydrophobicity can be obtained and there is no danger of a drop in the degree of crosslinking.

Heating may be carried out when forming the W/O emulsion. By heating, the solubility of the hydrophobizing agent can be increased, enabling it to be uniformized with the monovalent salt of alginic acid, and thus making it possible to stabilize the W/O emulsion. The heating temperature is preferably between 15° C. and 100° C., and more preferably between 40° C. and 80° C.

After the W/O emulsion has been formed, crosslinking treatment is carried out. Crosslinking treatment may be carried out by adding a polyvalent metal salt-containing solution to the W/O emulsion and stirring. Alternatively, crosslinking treatment may be carried out by adding the W/O emulsion to a polyvalent metal salt-containing solution and stirring. The polyvalent metal salt-containing solution used may be the same as that described above in the explanation of Method 2.

If necessary, crosslinking treatment may be carried out under heating. Heating may be carried out when adding the polyvalent metal salt-containing solution to the dispersion, may be carried out during stirring following addition, or may be carried out at both of these times. The heating temperature is preferably between 10° C. and 100° C., and more preferably between 15° C. and 80° C. The treatment time is preferably from 0.5 to 24 hours, and more preferably from 1 to 12 hours. By heating, the solubility of the hydrophobizing agent can be increased; in addition, the viscosity of the medium decreases, and so the hydrophobizing agent more readily penetrates to the interior of the particles.

Because a monovalent salt of alginic acid and a hydrophobizing agent are included in the aqueous phase of the above W/O emulsion, by carrying out crosslinking treatment, hydrophobization also is carried out at the same time.

After crosslinking treatment, if necessary, washing and drying of the particles may be carried out to obtain the hydrophobic alginic acid particles. Washing may be carried out by an ordinary method such as that of, for example, removing the solvent following crosslinking treatment, adding water and centrifuging. Drying may be carried out by an ordinary method such as spray drying, vacuum drying or freeze drying.

With Method 2 or Method 3, the hydrophobizing agent is deposited not only at the surface but can be made to penetrate to the interior as well, enabling particles of even greater hydrophobicity to be obtained.

If necessary, the hydrophobic alginic acid particles thus obtained may be subjected to surface treatment or grinding treatment using known equipment.

[Applications of Hydrophobic Alginic Acid Particles]

The hydrophobic alginic acid particles of the invention can be dispersed in water, a hydrophilic organic solvent, a hydrophobic organic solvent or a mixed solvent of these, and used as a dispersion.

The hydrophobic alginic acid particles of the invention can be used as an additive in liquids, paint coats, films, plate materials, and shaped articles of paper or the like. For example, it can be widely used in light-scattering agents and optical filter materials, colorants, cosmetics, absorbents, adsorbents, inks, adhesives, electromagnetic shielding materials, fluorescence sensors, biomarkers, recording materials, recording elements, polarizing materials, drug carriers for drug delivery systems (DDS), biosensors, DNA chips, diagnostic agents, thermally cavitated molded or formed products and anti-blocking agents.

The blocking of light or ultraviolet rays (UV) from entering a room, vehicle or the like with, for example, window glass products or interior goods such as curtains and wall materials serves not only to protect the human body from sunburns and other adverse effects but is useful as well by making it possible to prevent the deterioration of decorative articles, etc. within the room or vehicle.

The hydrophobic alginic acid particles of the invention are suitable as an additive for cosmetics. The chief ingredient comes from a naturally occurring polymer and the particles can be employed in liquid systems and other applications having a high oil content while enhancing, for example, the lightweight properties, feel, flow properties and solution dispersibility. Also, when the particle shape has recesses, the particles possess, on account of their distinctive shape, adhesive forces which differ from those of ordinary spherical particles. As a result, along with enabling improved light scattering properties, etc. to be obtained, they are effective for improving the bonding strength of pressed compacts of foundations and the like and also the holding power following application. In addition, the optical properties of the particles make the skin appear lighter and can enhance the covering power due to a shading effect. Also, on account of the slip characteristics distinctive to the particle shape, spread over the skin is excellent, wrinkles and pores can be made inconspicuous by finely filling in furrows in the skin texture, and the flowability of the overall product is freely controllable. The amount of addition, based on the overall product composition, is preferably from 0.1 to 50 wt %, and more preferably from 0.5 to 30 wt %. The light scattering properties such as the UV scattering effect and the shading effect, the flowability, the moldability, improvements in adhesion, the finished look and other qualities can be suitably adjusted according to the intended use/purpose. Based on investigations by the inventors, as an additive for cosmetics, addition in an amount of from 1 to 20 wt % is especially preferred. These particles may also be suitably adjusted and used in combination with commercially available particles.

Cosmetics in which the inventive particles provide highly advantageous effects include, in particular, skin care products, hair products, antiperspirants, Makeup products, UV protection products and scented products. Specific examples include base cosmetics such as milky emulsions, creams, lotions, calamine lotions, sunscreens, makeup bases, suntan lotions, aftershave lotions, preshave lotions, packs, cleansing materials, facial cleansers, cosmetics for acne, and essences; makeup cosmetics such as foundation, face powder, mascara, eye shadow, eyeliner, eyebrow, cheek, nail color, lip cream and lipstick; and also shampoos, rinses, conditioners, hair colors, hair tonics, setting agents, body powders, hair growth promoters, deodorants, depilatories, soaps, body shampoos, bath preparations, hand soaps and perfumes. The form of the product is not particularly limited and may be, for example, a liquid, emulsion, cream, solid, paste, gel, powder, multi-layer preparation, mousse or spray. The hydrophobic alginic acid particles of the invention can be expected to have useful effects as an additive for these cosmetics.

The hydrophobic alginic acid particles of the invention can be included as an additive in printing inks used in, for example, screen printing, offset printing, process printing, gravure printing, pad printing, coaters and inkjet printing; as an additive in inks used in writing implements such as marking pens, ballpoint pens, fountain pens, calligraphy pens and magic markers; and as an additive in writing materials such as crayons, artist's paints and erasers.

The hydrophobic alginic acid particles of the invention are suitable as an additive for paints and coatings that may be employed in, for example, brush painting, spray painting, electrostatic coating, electrodeposition coating, flow coating, roller coating and dip coating. For instance, they are suitable as additives for paints and coatings that may be used on transportation equipment such as automobiles, railway cars, helicopters, ships, bicycles, snowmobiles, ropeways, lifts, hovercrafts and motorcycles; building members such as window sashes, shutters, cisterns, doors, balconies, outside panels for construction, roofing, staircases, skylights and concrete walls; the exterior walls and interior finish on the inside and outside of buildings; roadway members such as guardrails, pedestrian bridges, sound insulating walls, road signs, highway sidewalls, elevated railway bridges, and bridges; industrial plant members such as tanks, pipes, towers and smokestacks; agricultural facilities such as PVC and other types of greenhouses, silos and agricultural sheeting; telecommunications facilities such as utility poles, transmission towers and parabolic antennas; electrical equipment such as electrical service boxes, lighting equipment, outdoor air conditioning units, washing machines, refrigerators and electric ranges, as well as covers for these; and other articles such as monuments, gravestones, paving materials, windscreens, waterproof sheeting and curing sheets for construction.

The form of the paint or coating is exemplified by not only solvent-based paints, but also aqueous dispersion paints, nonaqueous dispersion paints, powder paints and electrodeposition coatings, and may be suitably selected as needed.

EXAMPLES

Synthesis Examples, Practical Examples of the invention and Comparative Examples are given below by way of illustration, although the invention is not limited to these Examples. The particle size distributions and volume mean particle sizes (MW) in the Examples and Comparative Examples were measured using the MICROTRACK MT3000 (Nikkiso Co., Ltd.).

[1] Production of Particles

[Example 1-1] Production of A1 Particles

The ingredients shown below were charged into a 2,000 mL flask and dispersed by one hour of stirring using an agitator.

| | |
|---|---|
| Spherical calcium alginate beads (Flavikafine ™, from Nisshinbo Chemical Inc.; MV = 20 μm) | 194.0 g |
| Deionized water | 735.0 g |
| Ethanol | 315.0 g |
| Sodium laurate | 6.0 g |

Next, the dispersion was gradually heated on an oil bath and, after heating for 2 hours at 95° C., hydrophobization was carried out by administering surface treatment while removing the solvent by distillation and concentrating the reaction solution. After cooling, centrifugal washing with deionized water was repeatedly carried out, ultimately arriving at a 10 wt % aqueous dispersion. This dispersion was spray-dried (hot-air temperature, 220° C.) using a spray dryer, giving the target A1 Particles. The A1 Particles were examined under a scanning electron microscope (S-4800, from Hitachi High-Technologies Corporation; referred to below as the "SEM") and the shapes were checked, whereupon the particle size was substantially the same as before hydrophobization. In addition, the particle size distribution was checked by particle size distribution measurement and found to be the same as before hydrophobization, thus confirming that the particles were monodispersed and free of agglomeration. FIG. 1 shows a SEM micrograph (2,000×) of the A1 Particles.

[Example 1-2] Production of A2 Particles

The ingredients shown below were charged into a 5,000 mL heatable vessel and dispersed by one hour of stirring using an agitator.

| | |
|---|---|
| Sodium alginate (Kimika Algin ULV-L3 from Kimika Corporation; (40 mPa · s; 10 wt % aqueous solution)) | 313.6 g |
| Deionized water | 4,260.0 g |
| Sodium stearoyl glutamate | 6.4 g |

The dispersion was then heated to 60° C. and dissolution was carried out over two hours to prepare a 7.0 wt % aqueous solution. Next, the aqueous solution was spray-dried (hot-air temperature, 200° C.) using a spray dryer, thereby forming particles. The resulting particles were examined with the SEM and the shapes were checked, whereupon the particles were found to be flattened particles having recesses. These were monodispersed particles having a mean volumetric diameter (MV) of 7 μm.

Next, 300.0 g of the resulting particles was placed in 300.0 g of ethanol and stirred to give a 50.0 wt % ethanol dispersion, after which the dispersion was added dropwise under stirring to an already prepared 20.0 wt % aqueous solution of calcium chloride and crosslinking treatment was carried out. Stirring was continued for another 2 hours following the completion of dropwise addition.

Figure 2:
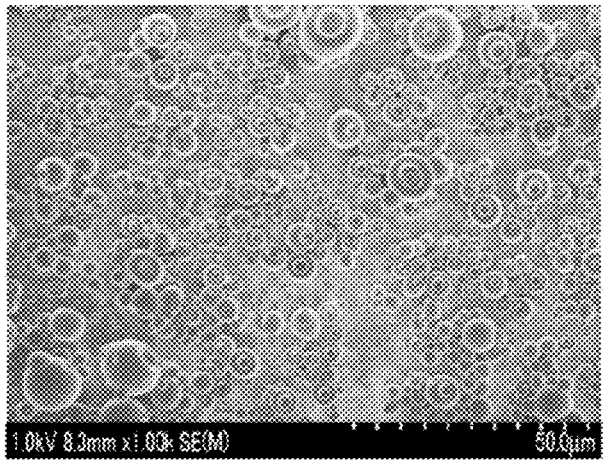
FIG. 2 shows a scanning electron micrograph (1,000×) of the particles obtained in Example 1-2.

Following the completion of stirring, centrifugal washing with deionized water was repeated, ultimately giving a 10 wt % aqueous dispersion. This dispersion was spray-dried using a spray Myer, giving the target A2 Particles. The A2 Particles were examined with the SEM and the shapes were checked, whereupon the particle size was substantially the same as before hydrophobization. In addition, the particle size distribution was checked by particle size distribution measurement and found to be the same as before hydrophobization, thus confirming that the particles were monodispersed and free of agglomeration. FIG. 2 shows a SEM micrograph (1,000×) of the A2 Particles.

[Example 1-3] Production of A3 Particles

The ingredients shown below were charged into a 5,000 mL heatable vessel, and emulsified by 5 minutes of stirring using a homogenizer (IKA T25).

| | |
|---|---|
| Sodium alginate (Kimika Algin ULV-L3G from Kimika Corporation; (20 mPa · s; 10 wt % aqueous solution)) | 200.0 g |
| Deionized water | 800.0 g |
| Hexane | 1,000.0 g |
| Sorbitan monooleate | 5.0 g |

A 15.0 aqueous solution of calcium chloride was added dropwise thereto. Following dropwise addition, 2 hours of stirring was carried out at 50° C. After stirring, the solution was cooled, repeatedly centrifugally washed with ethanol and deionized water, and then vacuum dried, giving the particles. The resulting particles were examined with the SEM and the shapes were checked, whereupon the particles were found to be spherical particles. As a result of particle size dispersion measurements, these were found to be monodispersed calcium alginate particles having an MV of 10 μm (referred to below as "Calcium Alginate A Particles").

Next, the ingredients shown below were charged into a 2,000 mL flask and dispersed by one hour of stirring using an agitator.

| | |
|---|---|
| Sodium Alginate A Particles | 142.5 g |
| Deionized water | 1,380.0 g |
| Ethanol | 345.0 g |
| Sodium stearate | 7.5 g |

Figure 3:
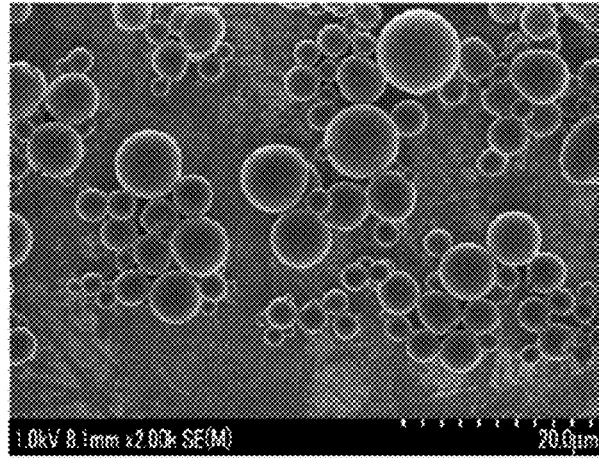
FIG. 3 shows a scanning electron micrograph (2,000×) of the particles obtained in Example 1-3.

Next, the dispersion was gradually heated on an oil bath and, after heating for 2 hours at 95° C., hydrophobization was carried out by administering surface treatment while removing the solvent by distillation and concentrating the reaction solution. After cooling, centrifugal washing with deionized water was repeatedly carried out, ultimately arriving at a 10 wt % aqueous dispersion. This dispersion was spray-dried (hot-air temperature, 200° C.) using a spray dryer, giving the target A3 Particles. The A3 Particles were examined under the SEM and the shapes were checked, whereupon the particle size was substantially the same as before hydrophobization. In addition, the particle size distribution was checked by particle size distribution measurement and found to be the same as before hydrophobization, thus confirming that the particles were monodispersed and free of agglomeration. FIG. 3 shows a SEM micrograph (2,000×) of the A3 Particles.

[Example 1-4] Production of A4 Particles

A 5,000 mL heatable vessel was charged with 1,725.0 g of deionized water and the temperature was raised to 50° C., following which 148.5 g of sodium alginate (available from Fuji Chemical Industries, Co. under the trade name Snow Algin SSL (40 mPa·s; 1 wt % aqueous solution)) and 1.5 g of sodium myristoyl glutamate were added and completely dissolved. A prepared solution of 12.0 g of sorbitan trioleate dissolved in 1,550.0 g of hexane was added thereto, and emulsification was carried out by 5 minutes of stirring using a homogenizer (IKA T25) while maintaining the temperature.

Next, the temperature was slowly raised to 65° C., following which a 20.0 wt % aqueous solution of calcium chloride was added dropwise. Following the completion of addition, stilling was carried out for another 2 hours while maintaining the temperature.

Following the completion of stirring, the system was cooled to room temperature and was then repeatedly centrifugally washed with ethanol and deionized water, ultimately giving a 10 wt % aqueous dispersion. This dispersion was spray-dried using a spray dryer (hot-air temperature, 200° C.), giving the target A4 Particles. The A4 Particles were examined with the SEM and the shapes were checked and found to be spherical particles. Particle size distribution measurements showed these to be monodispersed particles having an MV of 3 μm.

[Example 1-5] Production of A5 Particles

The ingredients shown below were charged into a 10,000 mL heatable vessel and dispersed using an agitator.

| | |
|---|---|
| Ammonium alginate (Kimika Algin NH-1 from Kimika Corporation; (35 mPa · s; 1 wt % aqueous solution)) | 50.0 g |
| Deionized water | 2,450.0 g |

The dispersion was then heated to 60° C. and dissolution was carried out over 3 hours to prepare a 2.0 wt % aqueous solution. The resulting solution was cooled, following which the aqueous solution was spray-dried using a spray dryer, thereby forming particles. The resulting particles were examined with the SEM and the shapes were checked, whereupon the particles were found to be flattened particles having recesses. These were monodispersed particles having an MV of 2 μm.

Next, 40.0 g of the resulting particles was placed in 60.0 g of ethanol and stirred to give a 40.0 wt % ethanol dispersion, after which the dispersion was added dropwise under stirring to an already prepared 10.0 wt % aqueous solution of calcium chloride and crosslinking treatment was carried out. Stirring was continued for another 2 hours following the completion of dropwise addition.

Following the completion of stirring, centrifugal washing with deionized water was repeatedly carried out, ultimately giving a 5.0 wt % ethanol dispersion. Triethoxy-n-octylsilane, 2.0 g, was added to this dispersion, following which the dispersion was spray-dried (hot-air temperature, 50° C.) using a spray dryer, giving the target A5 Particles. The A5 Particles were examined with the SEM and the shapes were checked, whereupon the particle size was substantially the same as before hydrophobization. In addition, the particle size distribution was checked by particle size distribution measurement, whereupon to the distribution was found to be the same as before hydrophobization, thus confirming that the particles were monodispersed and free of agglomeration.

[Example 1-6] Production of A6 Particles

The ingredients shown below were charged into a 5,000 mL flask and dissolved by 3 hours of stirring using an agitator.

| | |
|---|---|
| Potassium alginate (Kimika Algin ULV-L3 from Kimika Corporation; (40 mPa · s; 10 wt % aqueous solution)) | 285.0 g |
| Deionized water | 3,450.0 g |
| Sodium palmitate | 15.0 g |

The aqueous solution was spray-dried (hot-air temperature, 200° C.) using a spray dryer, thereby forming particles. The resulting particles were examined with the SEM and the shapes were checked, whereupon the particles were found to be spherical or approximately spherical particles. The particle size distribution was measured, as a result of which these were found to be monodispersed particles having an MV of 33 μm.

Next, 270.0 g of the resulting particles was placed in 330.0 g of ethanol and stirred to give a 45.0 wt % ethanol dispersion, after which the dispersion was added dropwise under stirring to an already prepared 20.0 wt % aqueous solution of calcium chloride and crosslinking treatment was carried out. Stirring was continued for another 3 hours following the completion of dropwise addition.

Following the completion of stirring, centrifugal washing with deionized water was repeatedly carried out, ultimately giving a 15 wt % aqueous dispersion. This dispersion was spray-dried using a spray dryer, giving the target A6 Particles. The A6 Particles were examined with the SEM and the shapes were checked, whereupon the particle size was substantially the same as before crosslinking treatment. In addition, the particle size distribution was checked by particle size distribution measurement, whereupon the distribution was found to be the same as before crosslinking treatment, thus confirming that the particles were monodispersed and free of agglomeration.

[Example 1-7] Production of A7 Particles

The ingredients shown below were charged into a 10,000 mL heatable vessel and dispersed using an agitator.

| | |
|---|---|
| Sodium alginate (Kimika Algin ULV-L3G from Kimika Corporation; (20 mPa · s; 10 wt % aqueous solution)) | 300.0 g |
| Deionized water | 5,700.0 g |

The dispersion was then heated to 60° C. and the sodium alginate was dissolved over a period of 2 hours, thereby preparing a 5.0 wt % aqueous solution.

The resulting solution was cooled and then spray-dried using a spray dryer, thereby forming particles. The resulting particles were examined with the SEM and the shapes were checked, whereupon the particles were found to be flattened particles having recesses. The particles were monodispersed particles having, in the particle size distribution, an MV of 5 μm.

Next, 280.0 g of the resulting particles was placed in 520.0 g of isopropyl alcohol and stirred to give a 35.0 wt % isopropyl alcohol dispersion, after which the dispersion was added dropwise under stirring to an already prepared 20.0 wt % aqueous solution of calcium chloride and crosslinking treatment was carried out. Stirring was continued for another 2 hours following the completion of dropwise addition.

Following the completion of stirring, centrifugal washing with deionized water was repeatedly carried out, ultimately giving a 10.0 wt % isopropyl alcohol dispersion. To this dispersion was added 9.8 g of trimethoxy(3,3,3-trifluoro-propyl)silane and spray-drying (hot-air temperature, 60° C.) was carried out using a spray dryer, giving the target A7 Particles. The A7 Particles were examined with the SEM and the shapes were checked, whereupon the particle size was substantially the same as before hydrophobization. In addition, the particle size distribution was checked by particle size distribution measurement and found to be the same as before hydrophobization, thus confirming that the particles were monodispersed and free of agglomeration.

Comparative Example 1-1

The spherical beads of calcium alginate used in Example 1-1 (Flavikafine™ from Nisshinbo Chemical Inc; MV=20 μm) were treated as the B1 Particles.

[Comparative Example 1-2] Production of B2 Particles

The ingredients shown below were charged into a 5,000 mL flask and dissolved by stirring for 2 hours using an agitator.

| | |
|---|---|
| Sodium alginate (Kimika Algin ULV-L3G from Kimika Corporation; (20 mPa · s; 10 wt % aqueous solution)) | 400.0 g |
| Deionized water | 3,600.0 g |

The resulting aqueous solution was spray-dried (hot-air temperature, 200° C.) using a spray dryer, giving the B2 Particles. The resulting particles were examined with the SEM and the shapes were checked, whereupon they were found to be spherical or approximately spherical particles. As a result of particle size distribution measurement, the particles were found to be monodispersed particles having an MV of 11 μm.

Comparative Example 1-3

The particles prior to crosslinking treatment obtained in the course of Example 1-2 were treated as the B3 Particles.

[Comparative Example 1-4] Production of B4 Particles

The ingredients shown below were charged all at once into a 2,000 mL flask and spherical polymer B4 Particles of methyl methacrylate alone having an average particle size of 5 μm were produced by the same method as in Comparative Example 1-3 in WO 2016/181877 A1.

| | |
|---|---|
| Water | 1,386.5 g |
| Methyl methacrylate | 173.4 g |
| Lauryl peroxide | 8.6 g |
| Polyvinyl pyrrolidone (K-30) | 17.3 g |

The shapes, chief raw materials, hydrophobizing agents and mean volumetric diameters (MV) of Particles A1 to A7 and B1 to B4 are shown collectively in Table 1.

TABLE 1

| | Particles | Chief raw material Hydrophobizing agent | Crosslinking | Main shape | MV (μm) | Hydrophobization |
|---|---|---|---|---|---|---|
| Example 1-1 | A1 | sodium alginate fatty acid salt | calcium-crosslinked | spherical | 20 | surface |
| Example 1-2 | A2 | sodium alginate amino acid salt | calcium-crosslinked | flattened with recesses | 7 | surface + interior |
| Example 1-3 | A3 | sodium alginate fatty acid salt | calcium-crosslinked | spherical | 10 | surface |
| Example 1-4 | A4 | sodium alginate amine acid Salt | calcium-crosslinked | sphetical | 3 | surface + interior |
| Exatnple 1-5 | A5 | ammonium alginate organosilicon compound | calcium-crosslinked | flattened with recesses | 2 | surface |
| Example 1-6 | A6 | Potassium alginate fatty acid salt | calcium-crosslinked | spherical, approx. spherical | 33 | surface + interior |
| Example 1-7 | A7 | sodium alginate fluorine compound | calcium-crosslinked | flattened with recesses | 5 | surface |
| Comparative Example 1-1 | B1 | sodium alginate | calcium-crosslinked | spherical | 20 | none |
| Comparative Example 1-2 | B2 | sodium alginate | uncrosslinked | spherical, approx. spherical | 11 | none |
| Comparative Example 1-3 | B3 | sodium alginate | uncrosslinked | flattened with recesses | 7 | surface + interior |
| Comparative Example 1-4 | B4 | methyl methacrylate | uncrosslinkcd | spherical | 5 | none |

[2] Measurement of Basic Properties

Examples 2-1 to 2-7, Comparative Examples 2-1 to 2-4

The water absorption and oil absorption of each of Particles A1 to A7 and B1 to B4 were measured by the following methods, and evaluations of their heat resistances, chemical resistances and hot chemical resistances were carried out as described below. The results are shown in Tables 2 and 3.

[Measurement of Oil Absorption]
The oil absorption was measured in general accordance with the boiled linseed oil method described in JIS K 5101.

[Measurement of Water Absorption]
Each type of particle, in an amount of 1 gram, was placed in a 500 mL beaker, following which 200 mL of deionized water was added and 30 minutes of suspension stirring (150 rpm, 25° C.) was carried out. The beaker contents were then transferred to a 500 ml, centrifuge tube and 30 minutes of centrifugation at 2,000G was carried out using a centrifuge (himac CR20GII, from Koki Holdings Co., Ltd.). Following centrifugation, the supernatant was gently discarded, the specimen was removed from the centrifuge tube and the weight was measured (We). The specimen was then dried to a constant weight in a 105° C. drying oven and the dry weight was measured ($D_w$). The water absorption was calculated using the following formula.

$$\text{Water absorption (mL/100 g)} = ((W_w - D_w)/D_w) \times 100$$

[Evaluation of Heat Resistance]
Each type of particle, in an amount of 0.5 g, was placed in an aluminum petri dish and heated for 2 hours at 180° C. in a drying oven, following which the particles were visually checked for melting, the particle shapes were checked by SEM and the heat resistance was evaluated according to the following criteria.

[Evaluation Criteria]
Visual: ○: No major change
Δ: Some melting
x: Melted
SEM: 1: Particle shapes are those of produced particles 2: Particle shapes are maintained, but surface melting is apparent in places
3: Partially melted, partial retention of particle shapes
4: No particle shapes apparent (completely melted)

[Evaluation of Chemical Resistance]
One gram of each type of particle and 99 g of the solvent shown in Table 3 were placed in a 300 mL flask (1 wt %) and stirred for 2 hours at room temperature (25° C.), following which the dispersed state of the particles was visually checked, the particle shapes were checked by SEM, and the chemical resistance was evaluated according to the following criteria.

[Evaluation of Hot Chemical Resistance]
One gram of each type of particle and 99 g of the solvent shown in Table 3 were placed in a 300 mL flask (1 wt %) and stirred for 2 hours at 70° C., following which the dispersed state of the particles was visually checked, the particle shapes were checked by SEM, and the hot chemical resistance evaluation was evaluated according to the following criteria.

[Evaluation Criteria]
◎: Visually, particles are dispersed; in SEM, particles are in shape of produced particles
○: Visually, particles are dispersed; in SEM, particle shapes are maintained, with surface melting apparent in places
Δ: Visually, particles are partially dispersed; in SEM, particles are deformed
x: Visually, particles have dissolved; in SEM, no particle shapes remain

TABLE 2

| | Particles | Heat resistance (Visual/ SEM) | Water absorption ($A_w$) (mL/100 g) | Oil absorption ($A_o$) (mL/100 g) | $A_w/A_o$ |
|---|---|---|---|---|---|
| Example 2-1 | A1 | ○/1 | 24 | 105 | 0.23 |
| Example 2-2 | A2 | ○/1 | 14 | 90 | 0.16 |
| Example 2-3 | A3 | ○/1 | 21 | 100 | 0.21 |
| Example 2-4 | A4 | ○/1 | 19 | 80 | 0.24 |
| Example 2-5 | A5 | ○/2 | 22 | 80 | 0.28 |
| Example 2-6 | A6 | ○/1 | 32 | 110 | 0.29 |

TABLE 2-continued

| | Particles | Heat resistance (Visual/ SEM) | Water absorption ($A_w$) (mL/100 g) | Oil absorption ($A_o$) (mL/100 g) | $A_w/A_o$ |
|---|---|---|---|---|---|
| Example 2-7 | A7 | ○/2 | 20 | 90 | 0.22 |
| Comparative Example 2-1 | B1 | ○/1 | 126 | 65 | 1.94 |
| Comparative Example 2-2 | B2 | ○/2 | dissolved | 60 | — |

TABLE 2-continued

| | Particles | Heat resistance (Visual/ SEM) | Water absorption ($A_w$) (mL/100 g) | Oil absorption ($A_o$) (mL/100 g) | $A_w/A_o$ |
|---|---|---|---|---|---|
| Comparative Example 2-3 | B3 | ○/2 | dissolved | 65 | — |
| Comparative Example 2-4 | B4 | x/4 | 25 | 75 | 0.33 |

TABLE 3

| | Particles | Water Room Temp. | Water 70° C. | Toluene Room Temp. | Toluene 70° C. | Ethyl acetate Room Temp. | Ethyl acetate 70° C. | DPG Room Temp. | DPG 70° C. | Ethanol Room Temp. | Ethanol 70° C. |
|---|---|---|---|---|---|---|---|---|---|---|---|
| Example 2-1 | A1 | ⊚ | ⊚ | ⊚ | ⊚ | ⊚ | ⊚ | ⊚ | ⊚ | ⊚ | ⊚ |
| Example 2-2 | A2 | ⊚ | ⊚ | ⊚ | ⊚ | ⊚ | ⊚ | ⊚ | ⊚ | ⊚ | ⊚ |
| Example 2-3 | A3 | ⊚ | ⊚ | ⊚ | ⊚ | ⊚ | ⊚ | ⊚ | ⊚ | ⊚ | ⊚ |
| Example 2-4 | A4 | ⊚ | ⊚ | ⊚ | ⊚ | ⊚ | ⊚ | ⊚ | ⊚ | ⊚ | ⊚ |
| Example 2-5 | A5 | ⊚ | ⊚ | ⊚ | ○ | ⊚ | ○ | ⊚ | ○ | ⊚ | ○ |
| Example 2-6 | A6 | ⊚ | ⊚ | ⊚ | ⊚ | ⊚ | ⊚ | ⊚ | ⊚ | ⊚ | ⊚ |
| Example 2-7 | A7 | ⊚ | ⊚ | ⊚ | ○ | ⊚ | ○ | ⊚ | ○ | ⊚ | ○ |
| Comparative Example 2-1 | B1 | ⊚ | ⊚ | ⊚ | ⊚ | ⊚ | ⊚ | ⊚ | ⊚ | ⊚ | ⊚ |
| Comparative Example 2-2 | B2 | X | X | ○ | ○ | ○ | ○ | ○ | ○ | ○ | Δ |
| Comparative Example 2-3 | B3 | X | X | ○ | ○ | ○ | ○ | ○ | ○ | ○ | Δ |
| Comparative Example 2-4 | B4 | ○ | ○ | X | X | X | X | Δ | X | ○ | ○ |

[3] Sensory Tests and Evaluation of Adhesion

Examples 3-1 to 3-7, Comparative Examples 3-1 to 3-4

Particles A1 to A7 and B1 to B4 were evaluated for feel, slip characteristics and particle adhesion by the methods described below. The results are shown in Table 4.

(1) Feel

The feel of each type of particle when spread over the skin was rated according to the criteria shown below.

(2) Slip Characteristics to One gram of each type of particle was placed on black synthetic leather and the length when spread by finger was rated according to the criteria shown below.

(3) Particle Adhesion

One gram of each type of particle was placed on black synthetic leather and uniformly spread with a powder puff, following which the leather was struck three times and the amount of particles remaining was examined with a digital microscope (VHX200, from Keyence Corporation) and rated according to the criteria shown below.

[Evaluation Criteria]

⊚: excellent

○: good

Δ: standard x: unacceptable

TABLE 4

| | Particles | Main shape | Hydrophobization | MV (μm) | Feel | Slip characteristics | Particle adhesion |
|---|---|---|---|---|---|---|---|
| Example 3-1 | A1 | spherical | yes | 20 | ○ | ⊚ | ○ |
| Example 3-2 | A2 | flattened with recesses | yes | 7 | ⊚ | ⊚ | ⊚ |

TABLE 4-continued

| | Particles | Main shape | Hydrophobization | MV (μm) | Feel | Slip characteristics | Particle adhesion |
|---|---|---|---|---|---|---|---|
| Example 3-3 | A3 | spherical | yes | 10 | ◎ | ○ | ○ |
| Example 3-4 | A4 | spherical | yes | 3 | ◎ | ○ | ◎ |
| Example 3-5 | A5 | flattened with recesses | yes | 2 | ○ | ◎ | ○ |
| Example 3-6 | A6 | spherical, approx. spherical | yes | 33 | ○ | ◎ | ○ |
| Example 3-7 | A7 | flattened with recesses | yes | 5 | ○ | ○ | ○ |
| Comparative Example 3-1 | B1 | spherical | no | 20 | X | Δ | Δ |
| Comparative Example 3-2 | B2 | spherical, approx. spherical | no | 11 | Δ | Δ | ○ |
| Comparative Example 3-3 | B3 | flattened with recesses | yes | 7 | ○ | Δ | Δ |
| Comparative Example 3-4 | B4 | spherical | no | 5 | ○ | ○ | ○ |

In terms of the feel and the slip characteristics, Particles A1 to A7, which were hydrophobized alginic acid particles, were at least comparable to Polymer Particle B4. As for particle adhesion, so long as they had a similar Particle size, Particles A1 to A7 were able to maintain a comparable adhesion. On the other hand, Particles B1 and B2, which were pot subjected to hydrophobization, tended to have somewhat diminished feel and slip characteristics owing to moisture absorption. Similarly, in the case of hydrophobized B3 particles, which were not crosslinked, owing to a worsening in the moisture absorption by the base particles, the feel and slip characteristics tended to be diminished. In the case of hydrophobic alginic acid Particles A1 and A6 having large particle sizes, the slip characteristics and adhesion were both relatively good.

[4] Test of Solubility in Aqueous Sodium Chloride Solution

Examples 4-1 to 4-7, Comparative Examples 4-1 to 4-4

Particles A1 to A-7 and B1 to B4 were each dispersed in water or an aqueous sodium chloride solution (sodium chloride concentration, 3 wt %) to a concentration of 0.1 wt %, and solubility tests were carried out.

(1) Appearance: The condition when 72 hours had elapsed following dispersion was visually checked.

(2) Shape: Changes in shape when 72 hours, 240 hours and 720 hours had elapsed following dispersion in an aqueous solution of sodium chloride, as compared with the shape prior to the test, were checked by measuring the particle size distribution.

(3) Transmittance: Letting S131, SD2 and SD3 be the respective percent transmittances to 560 μm wavelength light of a dispersion prepared by dispersing the particles in an aqueous solution of sodium chloride when 72 hours, 240 hours and 720 hours have elapsed following preparation, and letting WD1, WD2 and WD3 be the respective percent transmittances to 560 mi wavelength light of a dispersion prepared by dispersing the particles in water when 72 hours, 240 hours and 720 hours have elapsed following preparation, the ratios WD1/SD1, WD2/SD2 and WD3/SD3 were calculated. The transmittances were measured using a UV-visible spectrophotometer (UV-2450, from JASCO Corporation).

The results are shown in Table 5.

TABLE 5

| | Particles | Shape | | | Appearance | | Shape | SD | WD | WD/SD |
|---|---|---|---|---|---|---|---|---|---|---|
| | | | | | Water | Aqueous NaCl solution | | | | |
| Example 4-1 | A1 | spherical | | after 72 hrs | cloudy | clear | changed | 92 | 17 | 0.18 |
| | | | | after 240 hrs | cloudy | clear | changed | 91 | 16 | 0.18 |
| | | | | after 720 hrs | cloudy | clear | changed | 91 | 15 | 0.16 |
| Example 4-2 | A2 | flattened with reesses | | after 72 hrs | cloudy | clear | changed | 85 | 20 | 0.24 |
| | | | | after 240 hrs | cloudy | clear | changed | 85 | 17 | 0.20 |
| | | | | after 720 hrs | cloudy | clear | changed | 85 | 17 | 0.20 |
| Example 4-3 | A3 | spherical | | after 72 hrs | cloudy | clear | changed | 88 | 19 | 0.22 |
| | | | | after 240 hrs | cloudy | clear | changed | 88 | 18 | 0.20 |
| | | | | after 720 hrs | cloudy | clear | changed | 88 | 18 | 0.20 |
| Example 4-4 | A4 | spherical | | after 72 hrs | cloudy | clear | changed | 90 | 26 | 0.29 |
| | | | | after 240 hrs | cloudy | clear | changed | 89 | 20 | 0.22 |
| | | | | after 720 hrs | cloudy | clear | changed | 89 | 18 | 0.20 |
| Example 4-5 | A5 | flattened with recesses | | after 72 hrs | cloudy | translucent | changed | 86 | 31 | 0.37 |
| | | | | after 240 hrs | cloudy | clear | changed | 82 | 25 | 0.30 |
| | | | | after 720 hrs | cloudy | clear | changed | 82 | 18 | 0.22 |

TABLE 5-continued

|  |  |  |  | Appearance | | | | | |
|  |  |  |  | | Aqueous NaCl | | | | |
|  | Particles | Shape |  | Water | solution | Shape | SD | WD | WD/SD |
| --- | --- | --- | --- | --- | --- | --- | --- | --- | --- |
| Example 4-6 | A6 | spherical, | after 72 hrs | cloudy | clear | changed | 93 | 19 | 0.20 |
|  |  | approx. | after 240 hrs | cloudy | clear | changed | 93 | 18 | 0.19 |
|  |  | spherical | after 720 hrs | cloudy | clear | changed | 93 | 18 | 0.19 |
| Example 4-7 | A7 | flattened | after 72 hrs | cloudy | translucent | changed | 74 | 21 | 0.28 |
|  |  | with recesses | after 240 hrs | cloudy | clear | changed | 74 | 18 | 0.24 |
|  |  |  | after 720 hrs | cloudy | clear | changed | 74 | 18 | 0.24 |
| Comparative | B1 | spherical | after 72 hrs | cloudy | clear | changed | 91 | 12 | 0.13 |
| Example 4-1 |  |  | after 240 hrs | cloudy | clear | changed | 90 | 12 | 0.13 |
|  |  |  | after 720 hrs | cloudy | clear | changed | 90 | 12 | 0.13 |
| Comparative | B2 | spherical, | after 72 hrs | clear | clear | changed | 90 | 88 | 0.98 |
| Example 4-2 |  | approx. | after 240 hrs | clear | clear | changed | 90 | 88 | 0.98 |
|  |  | spherical | after 720 hrs | clear | clear | clanged | 90 | 88 | 0.98 |
| Comparative | B3 | flattened | after 72 hrs | clear | clear | changed | 86 | 85 | 0.99 |
| Example 4-3 |  | with recesses | after 240 hrs | clear | clear | changed | 85 | 84 | 0.99 |
|  |  |  | after 720 hrs | clear | clear | changed | 85 | 84 | 0.99 |
| Comparative | B4 | spherical | after 72 hrs | cloudy | cloudy | no change | 53 | 51 | 0.96 |
| Example 4-4 |  |  | after 240 hrs | cloudy | cloudy | no change | 53 | 51 | 0.96 |
|  |  |  | after 720 hrs | cloudy | cloudy | no change | 53 | 51 | 0.96 |

When the appearance and shape 0.05 hour after the start of the test were checked for Particles A1 to A7 and Particles B1 to B4, substantially no changes in appearance or shape, both in water and in the aqueous sodium chloride solution, were apparent for Particles A1 to A7. However, in the aqueous sodium chloride solution of Particle B1, in terms of appearance, the clarity increased and the shape also changed. From this, it was confirmed that the initial solubility of hydrophobic alginic acid Particles A1 to A7 in an aqueous sodium chloride solution is suppressed.

[5] Production and Evaluation of Optical Measurement Sheets

Examples 5-1 to 5-7, Comparative Examples 5-1 to 5-4

Optical measurement sheet-forming compositions were prepared by adding 35.0 g of a binder resin (a PVA resin from Kuraray Co., Ltd.) and 75.0 g of purified water to 15.0 g of, respectively, Particles A1 to A7 and B1 to B4 and mixing the ingredients together. The resulting compositions were then each coated onto one side of a 100 μm thick PET film (E-5000, from Toyobo Co., Ltd.) using a commercial bar coater. After coating, a drying oven was set to 60° C. and hot-air drying was carried out for 20 minutes, thereby producing Optical Sheets 1 to 11 having a coated layer thickness of 40 μm.

Using an automated goniophotometer (GP-200, from Murakami Color Research Laboratory Co., Ltd.), a fixed amount of light was irradiated onto each of Optical Sheets 1 to 11 at an incident angle of 45° and the light scattering distribution of the reflected light was measured. The light-diffusing performance of the sheet was evaluated according to the criteria shown below. The results are shown in Table 6.

[Evaluation Criteria]
Optical Sheet 11 (Polymer Particle B4) was used as the reference.
    A: Good diffusing ability
    B: Substantially the same diffusing ability
    C: Poor diffusing ability

TABLE 6

|  | Optical sheet | Particles | Main shape | Hydrophobization | Diffusion properties |
| --- | --- | --- | --- | --- | --- |
| Example 5-1 | 1 | A1 | spherical | yes | B |
| Example 5-2 | 2 | A2 | flattened with recesses | yes | A |
| Example 5-3 | 3 | A3 | spherical | yes | B |
| Example 5-4 | 4 | A4 | spherical | yes | A |
| Example 5-5 | 5 | A5 | flattened with recesses | yes | A |
| Example 5-6 | 6 | A6 | spherical, approx. spherical | yes | B |
| Example 5-7 | 7 | A5 | flattened with recesses | yes | B |
| Comparative Example 5-1 | 8 | B1 | spherical | no | C |
| Comparative Example 5-2 | 9 | B2 | spherical, approx. spherical | no | dissolved, viscosity rose, could not form a sheet |
| Comparative Example 5-3 | 10 | B3 | flattened with recesses | yes | dissolved, viscosity rose, could not form a sheet |
| Comparative Example 5-4 | 11 | B4 | spherical | no | reference |

It was confirmed that by carrying out hydrophobization, a performance comparable to or better ban general-purpose polymer particles call be obtained.

[6] Evaluation of Water Repellency

Examples 6-1 to 6-7, Comparative Examples 6-1 to 6-4

Coated Sheets 1 to 11 were produced by adding Particles A1 to A7 and B1 to B4 in respective amounts of 5 wt % to a commercial oil-based paint (Pro Touch, from Rock Paint Co., Ltd.), coating the resulting paints onto aluminum substrates and drying to form coats having a film thickness after drying of 2 μm.

The resulting coated sheets were visually evaluated for the presence or absence of light reflectivity and gloss, and a sensory evaluation of the tactile effect was carried out. The tactile effect was determined by running the fingers over the applied coat and evaluating the softness according to the criteria shown below. An aluminum substrate on which a coat had not been formed was used as the blank. The results are shown in Table 7.

[Evaluation Criteria]
○: Soft feel
Δ: Some softness can be felt
x: No softness

A both-sided tape was attached to an acrylic board, following which 1 mg/cm² of Particles A1 to A7 and B1 to B4 was weighed out onto the both-sided tape and uniformly applied with a powder puff. A water drop was dropped thereon and the contact angle 30 seconds later was measured using a contact angle goniometer (Drop Master 300, from Kyowa Interface Science Co., Ltd.). The results are shown in Table 8.

These results demonstrate that Coated Sheets 1 to 7 containing Particles A1 to A7 have a high hiding power and are capable of being used as a delustering agent.

TABLE 8

| | Sheet | Particles | Main shape | Hydro-phobi-zation | Contact angle (°) |
|---|---|---|---|---|---|
| Example 6-1 | 1 | A1 | spherical | yes | 109.5 |
| Example 6-2 | 2 | A2 | flattened with recesses | yes | 129 |
| Example 6-3 | 3 | A3 | spherical | yes | 112.5 |
| Example 6-4 | 4 | A4 | spherical | yes | 102 |
| Example 6-5 | 5 | A5 | flattened with recesses | yes | 96.5 |
| Example 6-6 | 6 | A6 | spherical, approx. spherical | yes | 88.5 |
| Example 6-7 | 7 | A7 | flattened with recesses | yes | 90.5 |
| Comparative Example 6-1 | 8 | B1 | spherical | no | 0 |
| Comparative Example 6-2 | 9 | B2 | spherical, approx. spherical | no | 0 |
| Comparative Example 6-3 | 10 | B3 | flattened with recesses | yes | 17.6 |
| Comparative Example 6-4 | 11 | B4 | spherical | no | 83.1 |

Sheets 1 to 7 to which Particles A1 to A7 were applied had large water drop contact angles, and were thus confirmed to have high water repellencies. On the other hand, because Particles B1 to B4 each exhibited a high hydrophilicity, as in the past, they are useful as hydrophilizing agents.

TABLE 7

| | Coated sheet | Particles | Main shape | Hydrophobization | Reflectivity (hiding power) | Gloss | Soft feel |
|---|---|---|---|---|---|---|---|
| Example 6-1 | 1 | A1 | spherical | yes | ○ | no | ○ |
| Example 6-2 | 2 | A2 | flattened with recesses | yes | ○ | no | ○ |
| Example 6-3 | 3 | A3 | spherical | yes | ○ | no | ○ |
| Example 6-4 | 4 | A4 | spherical | yes | ○ | no | ○ |
| Example 6-5 | 5 | A5 | flattened with recesses | yes | ○ | no | ○ |
| Example 6-6 | 6 | A6 | spherical, approx. spherical | yes | ○ | no | ○ |
| Example 6-7 | 7 | A7 | flattened with recesses | yes | ○ | no | ○ |
| Comparative Example 6-1 | 8 | B1 | spherical | no | ○ | no | Δ |
| Comparative Fysimple 6-2 | 9 | B2 | spherical, approx. spherical | no | Δ | somewhat glossy | Δ |
| Comparative Example 6-3 | 10 | B3 | flattened with recesses | yes | Δ | somewhat glossy | Δ |
| Comparative Example 6-4 | 11 | B4 | spherical | no | dissolved | dissolved | X |
| Blank | Al substrate | — | — | — | glossy | Yes | X |

[7] Production and Evaluation of Skin Cleansing Compositions

Examples 7-1 and 7-2, Comparative Example 7-1

Using Particles A1, A6 and B1, skin cleansing compositions (Cleansing Compositions 1 to 3) were produced according to the formulations shown in Table 9 below.

TABLE 9

| | | Example 7-1 Cleansing Composition 1 | Example 7-2 Cleansing Composition 2 | Comparative Example 7-1 Cleansing Composition 3 |
|---|---|---|---|---|
| Ingredient amounts (g) | Stearic acid | 2.0 | 2.0 | 2.0 |
| | Palmitic acid | 4.0 | 4.0 | 4.0 |
| | Myristic acid | 10.0 | 10.0 | 10.0 |
| | Lauric acid | 3.0 | 3.0 | 3.0 |
| | Lauramidopropylamine oxide | 20.0 | 20.0 | 20.0 |
| | Polypropylene glycol (400) | 2.0 | 2.0 | 2.0 |
| | Triethanolamine | 14.0 | 14.0 | 14.0 |
| | Ethylene glycol distearate | 1.0 | 1.0 | 1.0 |
| | Purified water | 41.0 | 41.0 | 41.0 |
| | Particle A1 | 3.0 | — | — |
| | Particle A6 | — | 3.0 | — |
| | Particle B1 | — | — | 3.0 |

Evaluations were carried out by the following methods on each of the cleansing compositions prepared. The results are shown in Table 10.

Ten people were selected as panelists and usage tests in which the skin cleansing compositions were used to cleanse the face were carried out. The six qualities of "Feeling on Use 1," "Feeling on Use 2," "Latherability," "Skin Cleansing and Exfoliating Effects," "Massaging Effects" and "Irritancy" were evaluated according to the criteria shown below, based on which each composition was rated overall as a face scrub.

Feeling on Use 1: Pleasantness of application and agreeability with the skin during use Feeling on Use 2: Absence of feeling of residual face scrub and skin tightness after rinsing off cleanser Latherability: Ease of foam production and foam longevity when cleanser is used Skin Cleansing and Exfoliating Effects:
Degree to which makeup comes off following use Massaging Effects: Do you feel any massaging effects, such as the resolution of dark patches on the skin, improvement in facial complexion and promotion of blood circulation?

Irritancy: Absence of redness, tingling, etc. after rinsing off cleanser

[Evaluation Criteria for Each Quality]

◎: Clearly effective (good feeling) [rated highly by 8 or more panelists]

○: Found to be effective (somewhat good feeling) [rated highly by 6 or 7 panelists]

□: Found to be effective (somewhat good feeling) [rated highly by 4 or 5 panelists]

Δ: Not very effective (somewhat poor feeling) [rated highly by 2 or 3 panelists]

x: Ineffective (poor feeling) [rated highly by no more than 1 panelist]

[Scoring Criteria]

◎: 8 points
○: 6 points
□: 4 points
Δ: 2 points
x: 0 points

[Overall Rating]

A: 36 points or more
B: 28 to 35 points
C: 20 to 27 points
D: 19 points or less

TABLE 10

| | Example 7-1 Cleansing Composition 1 | Example 7-2 Cleansing Composition 2 | Comparative Example 7-1 Cleansing Composition 3 |
|---|---|---|---|
| Feeling on Use 1 | ○ | ◎ | □ |
| Feeling on Use 2 | ○ | ○ | ○ |
| Latherability | ○ | ○ | Δ |
| Skin Cleansing and Exfoliating Effect | ○ | ◎ | ○ |
| Massaging Effect | □ | ○ | □ |
| Irritancy | ○ | ○ | □ |
| Score | 34 | 40 | 26 |
| Overall evaluation as face scrub | B | A | C |

As shown in Table 10, in terms of feeling and latherability as well, the hydrophobic alginic acid particles of the invention are also useful as an additive (basic ingredient) in body cleansing compositions.

[8] Production and Evaluation of Skin Care Preparations (1)

Examples 8-1 to 8-4 and Comparative Examples 8-1 and 8-2

Using Particles A2, A3, A4, A5, B1 and B4, makeup compositions (Foundations 1 to 6) were produced according to the formulations shown in Table 11 below.

TABLE 11

| | | Example 8-1 Foundation 1 | Example 8-2 Foundation 2 | Example 8-3 Foundation 3 | Example 8-4 Foundation 4 | Comparative Example 8-1 Foundation 5 | Comparative Example 8-2 Foundation 6 |
|---|---|---|---|---|---|---|---|
| Ingredient amounts (g) | Red iron oxide | 0.4 | 0.4 | 0.4 | 0.4 | 0.4 | 0.4 |
| | Yellow iron oxide | 1.0 | 1.0 | 1.0 | 1.0 | 1.0 | 1.0 |
| | Black iron oxide | 0.2 | 0.2 | 0.2 | 0.2 | 0.2 | 0.2 |
| | Titanium oxide | 7.0 | 7.0 | 7.0 | 7.0 | 7.0 | 7.0 |
| | Zinc oxide | 3.0 | 3.0 | 3.0 | 3.0 | 3.0 | 3.0 |
| | Silicone-treated large-particle-size titanium oxide | 3.0 | 3.0 | 3.0 | 3.0 | 3.0 | 3.0 |

TABLE 11-continued

| | Example 8-1 Foundation 1 | Example 8-2 Foundation 2 | Example 8-3 Foundation 3 | Example 8-4 Foundation 4 | Comparative Example 8-1 Foundation 5 | Comparative Example 8-2 Foundation 6 |
|---|---|---|---|---|---|---|
| Lauroyl lysine powder | 14.0 | 14.0 | 14.0 | 14.0 | 14.0 | 14.0 |
| Titanium mica | 4.0 | 4.0 | 4.0 | 4.0 | 4.0 | 4.0 |
| Talc | 37.97 | 37.97 | 37.97 | 37.97 | 37.97 | 37.97 |
| Methyl phenyl polysiloxane | 2.0 | 2.0 | 2.0 | 2.0 | 2.0 | 2.0 |
| Crystalline cellulose | 5.0 | 5.0 | 5.0 | 5.0 | 5.0 | 5.0 |
| Cornstarch | 10.0 | 10.0 | 10.0 | 10.0 | 10.0 | 10.0 |
| Methylparaben | 0.1 | 0.1 | 0.1 | 0.1 | 0.1 | 0.1 |
| Sodium dehydroacetate | 0.1 | 0.1 | 0.1 | 0.1 | 0.1 | 0.1 |
| Liquid paraffin | 1.5 | 1.5 | 1.5 | 1.5 | 1.5 | 1.5 |
| Butylene glycol | 0.5 | 0.5 | 0.5 | 0.5 | 0.5 | 0.5 |
| Coix seed extract | 0.1 | 0.1 | 0.1 | 0.1 | 0.1 | 0.1 |
| Carrot extract | 0.1 | 0.1 | 0.1 | 0.1 | 0.1 | 0.1 |
| Ubiquinone | 0.03 | 0.03 | 0.03 | 0.03 | 0.03 | 0.03 |
| Particle A2 | 10.0 | — | — | — | — | — |
| Particle A3 | — | 10.0 | — | — | — | — |
| Particle A4 | — | — | 10.0 | — | — | — |
| Particle A5 | — | — | — | 10.0 | — | — |
| Particle B1 | — | — | — | — | 10.0 | — |
| Particle B4 | — | — | — | — | — | 10.0 |

Fifteen people were selected as panelists and the feeling during use and the difference before and after use for Foundations 1 to 6 were evaluated overall in terms of the following five qualities: "adherence to skin," "good fit when applied," "sensation during use," "soft focus effect" and "durability of cosmetic effect (4 hours)," based on which the acceptability of the cosmetic formulations was assessed as A to G below.

A: Foundation 1 was best
B: Foundation 2 was best
C: Foundation 3 was best
D: Foundation 4 was best
E: Foundation 5 was best
F: Foundation 6 was best
G: They were all the same As a result, the assessments by the panelists were as follows:

A: 4 panelists
B: 2 panelists
C: 5 panelists
D: 3 panelists
E: 0 panelists
F: 1 panelist
G: 0 panelists Most of the panelists thought that Foundations 1 and 3 were particularly outstanding with respect to "adherence to skin," "soft focus effect" and "durability of cosmetic effect (4 hours)," and that the overall finish was good. Foundations 1 to 4 were preferred with regard to the "good fit when applied" and the "sensation during use." Although there was some difference of opinion, most of the panelists thought that, owing to the reduced particle size and the fact that the particles have been hydrophobized, use is possible at a level of performance comparable to or better than the polymer ingredient in Foundation 6. As for Foundation 5, most of the panelists thought that the "adherence to skin" and the "sensation during use" were somewhat lacking. These results demonstrate that the alginic acid particles of the invention can, as a cosmetics ingredient as well, exhibit properties comparable to or better than existing alginic acid particles.

[9] Production and Evaluation of Skin Care Preparations (2)

Examples 9-1 to 9-4 and Comparative Examples 9-1 and 9-2

Using Particles A2, A3, A4, A5, B1 and B4, makeup compositions (Liquid Foundations 7 to 12) were produced according to the formulations shown in Table 12 below.

TABLE 12

| | | Example 9-1 Foundation 7 | Example 9-2 Foundation 8 | Example 9-3 Foundation 9 | Example 9-4 Foundation 10 | Comparative Example 9-1 Foundation 11 | Comparative Example 9-2 Foundation 12 |
|---|---|---|---|---|---|---|---|
| Ingredient amounts (g) | 2% Acrylic acid-alkyl methacrylate copolymer dispersion | 15 | 15 | 15 | 15 | 15 | 15 |
| | 2% Carboxyvinyl polymer dispersion | 15 | 15 | 15 | 15 | 15 | 15 |
| | Dipropylene glycol | 5 | 5 | 5 | 5 | 5 | 5 |
| | Disodium edetate | 0.05 | 0.05 | 0.05 | 0.05 | 0.05 | 0.05 |
| | Purified water | 2.7 | 2.7 | 2.7 | 2.7 | 2.7 | 2.7 |
| | Ethanol | 15 | 15 | 15 | 15 | 15 | 15 |
| | Sorbitan monoisostearate | 2 | 2 | 2 | 2 | 2 | 2 |
| | Polyoxyethylene (2) $C_{12-16}$ alkyl ether phosphate | 0.5 | 0.5 | 0.5 | 0.5 | 0.5 | 0.5 |
| | 2-Ethylhexyl hydroxystearate | 5 | 5 | 5 | 5 | 5 | 5 |
| | Methylcyclopolysiloxane | 5 | 5 | 5 | 5 | 5 | 5 |
| | 2-Amino-2-methyl-1-propanol | 0.5 | 0.5 | 0.5 | 0.5 | 0.5 | 0.5 |
| | Titanium oxide | 10 | 10 | 10 | 10 | 10 | 10 |
| | Red iron oxide | 0.2 | 0.2 | 0.2 | 0.2 | 0.2 | 0.2 |

TABLE 12-continued

|  | Example 9-1 Foundation 7 | Example 9-2 Foundation 8 | Example 9-3 Foundation 9 | Example 9-4 Foundation 10 | Comparative Example 9-1 Foundation 11 | Comparative Example 9-2 Foundation 12 |
|---|---|---|---|---|---|---|
| Yellow iron oxide | 1 | 1 | 1 | 1 | 1 | |
| Black iron oxide | 0.1 | 0.1 | 0.1 | 0.1 | 0.1 | 0.1 |
| Talc | 3.7 | 3.7 | 3.7 | 3.7 | 3.7 | 3.7 |
| Crosslinked silicone powder | 1.5 | 1.5 | 1.5 | 1.5 | 1.5 | 1.5 |
| 2% Xanthan gum dispersion | 15 | 15 | 15 | 15 | 15 | 15 |
| Phenoxyethanol | 0.2 | 0.2 | 0.2 | 0.2 | 0.2 | 0.2 |
| Sodium dehydroacetate | 0.05 | 0.05 | 0.05 | 0.05 | 0.05 | 0.05 |
| Particle A2 | 1.0 | — | — | — | — | — |
| Particle A3 | — | 2.5 | — | — | — | — |
| Particle A4 | 1.5 | — | 2.5 | 1 | — | — |
| Particle A5 | — | — | — | 1.5 | — | — |
| Particle B1 | — | — | — | — | 2.5 | — |
| Particle B4 | — | — | — | — | — | 2.5 |

Fifteen people were selected as panelists, and the feeling during use and the difference before and after use for Foundations 7 to 12 were evaluated overall in terms of the following five qualities: "adherence to skin," "good fit when applied," "sensation during use," "soft focus effect" and "durability of cosmetic effect (4 hours)," based on which the acceptability of the cosmetic formulations was assessed as A to G below.

A: Foundation 7 was best
B: Foundation 8 was best
C: Foundation 9 was best
D: Foundation 10 was best
E: Foundation 11 was best
F: Foundation 12 was best
G: They were all the same As a result, the assessments by the panelists were as follows:

A: 5 panelists
B: 3 panelists
C: 4 panelists
D: 2 panelists
E: 0 panelists
F: 1 panelist
G: 0 panelists Most of the panelists thought that, with respect to "adherence to skin," "good fit when applied," "sensation during use," "soft focus effect" and "durability of cosmetic effect (4 hours)," Foundations 7 to 10 had a good overall finish. In particular, Foundations 7 to 10 were preferred and, although there was some difference of opinion, most thought that, in terms of conferring smoothness due to hydrophobization, the "good fit when applied" and the "sensation during use" are good. In addition, some were of the opinion that the handleability of emulsification, stabilizability and dispersibility were excellent, and most thought that use is possible at a level of performance comparable to or better than the polymer ingredient in conventional Foundation 12. On the other hand, most of the panelists thought that the "adherence to skin," "good fit when applied" and "sensation during use" were somewhat lacking in Foundation 11. These results demonstrate that the alginic acid particles of the invention are able, as an ingredient in liquid cosmetics as well, to exhibit properties comparable to or better than existing alginic acid particles.

As shown above, the hydrophobic alginic acid particles of the invention contain little extraneous matter such as agglomerates and can be stably and efficiently produced. Also, because crosslinkable particles that are heat resistant and resistant to (hot) chemicals can also be stably produced, use in various applications is possible.

Moreover, as particles that are size-controlled and environmentally friendly, particularly as a natural polymer-based soluble ingredient which is useful as a measure against marine pollution, the hydrophobic alginic acid particles of the invention can be effectively used in applications for which, depending on the intended use, environmental compatibility is required, such as paints, inks, molded articles, cosmetics, and thermally cavitated molded or formed products.

[10] Production of Various Skin Care Preparations

Given the large number of applications and products in cosmetics overall, particularly as skin care preparations, tests based on generally disclosed cosmetic formulations were conducted to determine whether it is possible to use the alginic acid Particles of the invention in cosmetics and skin care preparations. As a result, it was confirmed that the alginic acid particles of the invention compare favorably with and can be handled in the same way as existing polymer particles and inorganic particles.

Example formulations are presented below of skin care preparations that contain hydrophobic alginic acid particles of the invention. Using Particles A1 to A5, skin care preparations having the compositions shown in Tables 13 to 19 below were produced. Numbers in the tables indicate the content (wt %) of the ingredients.

(1) Powder Cosmetics

TABLE 13

| Powder Foundations | | Formulation Example | | | | | |
|---|---|---|---|---|---|---|---|
| | | 1 | 2 | 3 | 4 | 5 | 6 |
| Ingredients (wt %) | N-Lauroyl lysine-treated red iron oxide | 1.0 | 1.0 | 1.0 | 1.0 | 1.0 | 1.0 |
| | N-Lauroyl lysine-treated-treated yellow iron oxide | 4.0 | 4.0 | 4.0 | 4.0 | 4.0 | 4.0 |
| | N-Lauroyl lysine-treated-treated black iron oxide | 0.5 | 0.5 | 0.5 | 0.5 | 0.5 | 0.5 |
| | N-Lauroyl lysine-treated-treated titanium oxide | 7.0 | 7.0 | 7.0 | 7.0 | 7.0 | 7.0 |
| | N-Lauroyl lysine-treated strongly aggregated titanium oxide | 7.0 | 7.0 | 7.0 | 7.0 | 7.0 | 7.0 |

TABLE 13-continued

| Powder Foundations | Formulation Example | | | | | |
|---|---|---|---|---|---|---|
| | 1 | 2 | 3 | 4 | 5 | 6 |
| Hydrated silica/aluminum oxide silicone-treated finely divided titanium oxide | 2.0 | 2.0 | 2.0 | 2.0 | 2.0 | 2.0 |
| N-Lauroyl lysine-treated sericite | 30.06 | 30.06 | 30.06 | 30.06 | 30.06 | 30.06 |
| Zinc myristate-treated synthetic phlogopite | 15.0 | 15.0 | 15.0 | 15.0 | 15.0 | 15.0 |
| Boron nitride | 5.0 | 5.0 | 5.0 | 5.0 | 5.0 | 5.0 |
| Silicone-treated hemp cellulose powder | 10.0 | 10.0 | 10.0 | 10.0 | 10.0 | 10.0 |
| Chlorphenesin | 0.1 | 0.1 | 0.1 | 0.1 | 0.1 | 0.1 |
| Sodium dehydroacetate | 0.1 | 0.1 | 0.1 | 0.1 | 0.1 | 0.1 |
| Methyl polysiloxane | 4.0 | 4.0 | 4.0 | 4.0 | 4.0 | 4.0 |
| Diisostearyl malate | 1.5 | 1.5 | 1.5 | 1.5 | 1.5 | 1.5 |
| Glyceryl tri(2-ethylhexanoate) | 2.0 | 2.0 | 2.0 | 2.0 | 2.0 | 2.0 |
| Glyceryl tri(caprylate caprate myristate stearate) | 0.5 | 0.5 | 0.5 | 0.5 | 0.5 | 0.5 |
| 2-Ethylhexyl p-methoxycinnamate | 3.0 | 3.0 | 3.0 | 3.0 | 3.0 | 3.0 |
| Water-soluble collagen solution | 0.1 | 0.1 | 0.1 | 0.1 | 0.1 | 0.1 |
| Orchid extract | 0.01 | 0.01 | 0.01 | 0.01 | 0.01 | 0.01 |
| Royal jelly extract | 0.01 | 0.01 | 0.01 | 0.01 | 0.01 | 0.01 |
| Hydrolyzed conchiolin solution | 0.01 | 0.01 | 0.01 | 0.01 | 0.01 | 0.01 |
| *Rubus suavissimus* extract | 0.01 | 0.01 | 0.01 | 0.01 | 0.01 | 0.01 |
| Silk extract | 0.1 | 0.1 | 0.1 | 0.1 | 0.1 | 0.1 |
| Urethane powder | 2.0 | 2.0 | 2.0 | 2.0 | 2.0 | 2.0 |
| Particle A1 | 2.5 | — | — | — | — | 1.0 |
| Particle A2 | 1.5 | 5.0 | — | — | — | 1.0 |
| Particle A3 | — | — | 5.0 | — | — | 1.0 |
| Particle A4 | 1.0 | — | — | 5.0 | — | 1.0 |
| Particle A5 | — | — | — | — | 5.0 | 1.0 |

TABLE 14

| | Loose Face Powders | Formulation Example | | | | | |
|---|---|---|---|---|---|---|---|
| | | 7 | 8 | 9 | 10 | 11 | 12 |
| Ingredients (wt %) | Red iron oxide | 0.2 | 0.2 | 0.2 | 0.2 | 0.2 | 0.2 |
| | Yellow iron oxide | 0.1 | 0.1 | 0.1 | 0.1 | 0.1 | 0.1 |
| | Ultramarine | 0.05 | 0.05 | 0.05 | 0.05 | 0.05 | 0.05 |
| | Branched silicone/methyl hydrogen polysiloxane-treated titanium oxide | 2.0 | 2.0 | 2.0 | 2.0 | 2.0 | 2.0 |
| | Acicular titanium oxide | 3.0 | 3.0 | 3.0 | 3.0 | 3.0 | 3.0 |
| | Silicone-treated finely divided zinc oxide | 1.0 | 1.0 | 1.0 | 1.0 | 1.0 | 1.0 |
| | Fluorine compound-treated synthetic phlogopite | 5.0 | 5.0 | 5.0 | 5.0 | 5.0 | 5.0 |
| | Silicone-treated mica | 10.0 | 10.0 | 10.0 | 10.0 | 10.0 | 10.0 |
| | Talc | 67.65 | 67.65 | 67.65 | 67.65 | 67.65 | 67.65 |
| | Silica | 0.3 | 0.3 | 0.3 | 0.3 | 0.3 | 0.3 |
| | Methylparaben | 0.1 | 0.1 | 0.1 | 0.1 | 0.1 | 0.1 |
| | Ethylparaben | 0.1 | 0.1 | 0.1 | 0.1 | 0.1 | 0.1 |
| | Liquid paraffin | 1.5 | 1.5 | 1.5 | 1.5 | 1.5 | 1.5 |
| | 2-Ethylhexyl p-methoxycinnamate | 2.0 | 2.0 | 2.0 | 2.0 | 2.0 | 2.0 |
| | Urethane powder | 5.0 | 5.0 | 5.0 | 5.0 | 5.0 | 5.0 |
| | Particle A1 | 2.0 | — | — | — | — | — |
| | Particle A2 | — | 2.0 | — | — | — | 1.0 |
| | Particle A3 | — | — | 2.0 | — | — | — |
| | Particle A4 | — | — | — | 2.0 | — | 1.0 |
| | Particle A5 | — | — | — | — | 2.0 | — |

(2) Oil-Based Cosmetics

TABLE 15

| | Lipsticks | Formulation Example | | | | | |
|---|---|---|---|---|---|---|---|
| | | 13 | 14 | 15 | 16 | 17 | 18 |
| Ingredients (wt %) | Paraffin wax | 3.0 | 3.0 | 3.0 | 3.0 | 3.0 | 3.0 |
| | Synthetic hydrocarbon wax | 3.0 | 3.0 | 3.0 | 3.0 | 3.0 | 3.0 |
| | Ethylene-propylene copolymer | 3.0 | 3.0 | 3.0 | 3.0 | 3.0 | 3.0 |
| | Ceresin | 3.0 | 3.0 | 3.0 | 3.0 | 3.0 | 3.0 |
| | Microcrystalline wax | 3.0 | 3.0 | 3.0 | 3.0 | 3.0 | 3.0 |
| | Petrolatum | 5.0 | 5.0 | 5.0 | 5.0 | 5.0 | 5.0 |
| | Heavy liquid isoparaffin | 25.0 | 25.0 | 25.0 | 25.0 | 25.0 | 25.0 |

TABLE 15-continued

| | Formulation Example | | | | | |
|---|---|---|---|---|---|---|
| Lipsticks | 13 | 14 | 15 | 16 | 17 | 18 |
| Di(octyldodecyl/phytosteryl/behenyl) lauroyl glutamate | 10.0 | 10.0 | 10.0 | 10.0 | 10.0 | 10.0 |
| Polyglyceryl triisostearate | 5.0 | 5.0 | 5.0 | 5.0 | 5.0 | 5.0 |
| Octyl dodecanol | 5.0 | 5.0 | 5.0 | 5.0 | 5.0 | 5.0 |
| Squalane | 5.0 | 5.0 | 5.0 | 5.0 | 5.0 | 5.0 |
| Hydrogenated polydecene | 5.0 | 5.0 | 5.0 | 5.0 | 5.0 | 5.0 |
| Glyceryl Tri(caprylate/caprate) | 13.6 | 13.6 | 13.6 | 13.6 | 13.6 | 13.6 |
| Tocopherol | 0.1 | 0.1 | 0.1 | 0.1 | 0.1 | 0.1 |
| Red No. 201 | 0.1 | 0.1 | 0.1 | 0.1 | 0.1 | 0.1 |
| Red No. 202 | 0.1 | 0.1 | 0.1 | 0.1 | 0.1 | 0.1 |
| Acicular titanium oxide | 1.0 | 1.0 | 1.0 | 1.0 | 1.0 | 1.0 |
| Iron oxide | 0.5 | 0.5 | 0.5 | 0.5 | 0.5 | 0.5 |
| Silica | 3.0 | 3.0 | 3.0 | 3.0 | 3.0 | 3.0 |
| Mica | 2.0 | 2.0 | 2.0 | 2.0 | 2.0 | 2.0 |
| Titanium mica | 1.5 | 1.5 | 1.5 | 1.5 | 1.5 | 1.5 |
| Titanium oxide-coated glass flakes | 2.0 | 2.0 | 2.0 | 2.0 | 2.0 | 2.0 |
| Raspberry extract | 0.1 | 0.1 | 0.1 | 0.1 | 0.1 | 0.1 |
| Particle A1 | 0.5 | — | — | — | — | — |
| Particle A2 | 0.5 | 1.0 | — | — | — | 0.5 |
| Particle A3 | — | — | 1.0 | — | — | — |
| Particle A4 | — | — | — | 1.0 | — | 0.5 |
| Particle A5 | — | — | — | — | 1.0 | — |

TABLE 16

| | | Formulation Example | | | | | |
|---|---|---|---|---|---|---|---|
| | Lip coats | 19 | 20 | 21 | 22 | 23 | 24 |
| Ingredients (wt %) | Dextrin palmitate | 10.0 | 10.0 | 10.0 | 10.0 | 10.0 | 10.0 |
| | Heavy liquid isoparaffin | 50.0 | 50.0 | 50.0 | 50.0 | 50.0 | 50.0 |
| | Di(phytosteryl 2-octyl dodecyl) lauroyl glutamate | 10.0 | 10.0 | 10.0 | 10.0 | 10.0 | 10.0 |
| | Polyglyceryl diisostearate | 10.0 | 10.0 | 10.0 | 10.0 | 10.0 | 10.0 |
| | Diisostearyl malate | 14.3 | 14.3 | 14.3 | 14.3 | 14.3 | 14.3 |
| | Tocopherol | 0.1 | 0.1 | 0.1 | 0.1 | 0.1 | 0.1 |
| | Red No. 218 | 0.1 | 0.1 | 0.1 | 0.1 | 0.1 | 0.1 |
| | Yellow No. 4 aluminum lake | 0.5 | 0.5 | 0.5 | 0.5 | 0.5 | 0.5 |
| | Synthetic phlogopite | 1.0 | 1.0 | 1.0 | 1.0 | 1.0 | 1.0 |
| | Acicular titanium oxide | 0.5 | 0.5 | 0.5 | 0.5 | 0.5 | 0.5 |
| | Titanium oxide-coated glass flakes | 3.0 | 3.0 | 3.0 | 3.0 | 3.0 | 3.0 |
| | Particle A1 | 0.5 | — | — | — | — | — |
| | Particle A2 | — | 0.5 | — | — | — | 0.3 |
| | Particle A3 | — | — | 0.5 | — | — | 0.2 |
| | Particle A4 | — | — | — | 0.5 | — | — |
| | Particle A5 | — | — | — | — | 0.5 | — |

(3) Oil-In-Water Emulsified Cosmetics

TABLE 17

| | | Formulation Example | | | | | |
|---|---|---|---|---|---|---|---|
| | Mascaras | 25 | 26 | 27 | 28 | 29 | 30 |
| Ingredients (wt %) | Purified water | 43.9 | 43.9 | 43.9 | 43.9 | 43.9 | 43.9 |
| | Bentonite | 1.5 | 1.5 | 1.5 | 1.5 | 1.5 | 1.5 |
| | Phenoxyethanol | 0.5 | 0.5 | 0.5 | 0.5 | 0.5 | 0.5 |
| | Hydroxyethyl-cellulose | 2.0 | 2.0 | 2.0 | 2.0 | 2.0 | 2.0 |
| | Sericite | 0.5 | 0.5 | 0.5 | 0.5 | 0.5 | 0.5 |
| | PEG-20 glyceryl stearate | 5.0 | 5.0 | 5.0 | 5.0 | 5.0 | 5.0 |
| | Butylene glycol | 6.0 | 6.0 | 6.0 | 6.0 | 6.0 | 6.0 |
| | Boron nitride | 12.0 | 12.0 | 12.0 | 12.0 | 12.0 | 12.0 |
| | Iron oxide | 2.0 | 2.0 | 2.0 | 2.0 | 2.0 | 2.0 |
| | Titanium oxide | 1.0 | 1.0 | 1.0 | 1.0 | 1.0 | 1.0 |
| | Triethanolamine | 1.0 | 1.0 | 1.0 | 1.0 | 1.0 | 1.0 |
| | Carnauba wax | 1.0 | 1.0 | 1.0 | 1.0 | 1.0 | 1.0 |
| | Beeswax | 6.5 | 6.5 | 6.5 | 6.5 | 6.5 | 6.5 |
| | Cetanol | 2.0 | 2.0 | 2.0 | 2.0 | 2.0 | 2.0 |

TABLE 17-continued

| | Formulation Example | | | | | |
|---|---|---|---|---|---|---|
| Mascaras | 25 | 26 | 27 | 28 | 29 | 30 |
| Stearic acid | 2.0 | 2.0 | 2.0 | 2.0 | 2.0 | 2.0 |
| Polyisobutene | 1.0 | 1.0 | 1.0 | 1.0 | 1.0 | 1.0 |
| Tocopherol acetate | 0.1 | 0.1 | 0.1 | 0.1 | 0.1 | 0.1 |
| Acrylates copolymer | 9.0 | 9.0 | 9.0 | 9.0 | 9.0 | 9.0 |
| Particle A1 | 1.5 | — | — | — | — | — |
| Particle A2 | 1.5 | 3.0 | — | — | — | 1.0 |
| Particle A3 | — | — | 3.0 | — | — | 1.0 |
| Particle A4 | — | — | — | 3.0 | — | 1.0 |
| Particle A5 | — | — | — | — | 3.0 | — |

(4) Water-In-Oil Emulsified Cosmetics, Etc.

TABLE 18

| Water-in-Oil Foundations | | Formulation Example | | | | | |
|---|---|---|---|---|---|---|---|
| | | 31 | 32 | 33 | 34 | 35 | 36 |
| Ingredients (wt %) | Diglyceryl monoisostearate | 1.0 | 1.0 | 1.0 | 1.0 | 1.0 | 1.0 |
| | Polyether-modified silicone mixture | 5.0 | 5.0 | 5.0 | 5.0 | 5.0 | 5.0 |
| | Volatile silicone | 15.0 | 15.0 | 15.0 | 15.0 | 15.0 | 15.0 |
| | Isododecane | 5.0 | 5.0 | 5.0 | 5.0 | 5.0 | 5.0 |
| | Dipentaerythrityl tripolyhydroxystearate | 3.0 | 3.0 | 3.0 | 3.0 | 3.0 | 3.0 |
| | Liquid paraffin | 6.0 | 6.0 | 6.0 | 6.0 | 6.0 | 6.0 |
| | Soybean lecithin | 0.1 | 0.1 | 0.1 | 0.1 | 0.1 | 0.1 |
| | Propylene glycol dicaprylate | 4.0 | 4.0 | 4.0 | 4.0 | 4.0 | 4.0 |
| | Glycerin | 3.0 | 3.0 | 3.0 | 3.0 | 3.0 | 3.0 |
| | Maltitol | 3.0 | 3.0 | 3.0 | 3.0 | 3.0 | 3.0 |
| | Carrot extract | 0.1 | 0.1 | 0.1 | 0.1 | 0.1 | 0.1 |
| | *Sambucus nigra* flower extract | 0.1 | 0.1 | 0.1 | 0.1 | 0.1 | 0.1 |
| | Octyltriethoxysilane-treated titanium oxide | 10.0 | 10.0 | 10.0 | 10.0 | 10.0 | 10.0 |
| | Octyltriethoxysilane-treated red iron oxide | 0.2 | 0.2 | 0.2 | 0.2 | 0.2 | 0.2 |
| | Octyltriethoxysilane-treated yellow iron oxide | 0.8 | 0.8 | 0.8 | 0.8 | 0.8 | 0.8 |
| | Octyltriethoxysilane-treated black iron oxide | 0.1 | 0.1 | 0.1 | 0.1 | 0.1 | 0.1 |
| | Talc | 0.9 | 0.9 | 0.9 | 0.9 | 0.9 | 0.9 |
| | Purified water | 40.85 | 40.85 | 40.85 | 40.85 | 40.85 | 40.85 |
| | Sodium dehydroacetate | 0.05 | 0.05 | 0.05 | 0.05 | 0.05 | 0.05 |
| | Phenoxyethanol | 0.3 | 0.3 | 0.3 | 0.3 | 0.3 | 0.3 |
| | Crosslinked silicone powder | 0.5 | 0.5 | 0.5 | 0.5 | 0.5 | 0.5 |
| | Particle A1 | 1.0 | — | — | — | — | — |
| | Particle A2 | — | 1.0 | — | — | — | 0.5 |
| | Particle A3 | — | — | 1.0 | — | — | — |
| | Particle A4 | — | — | — | 1.0 | — | 0.5 |
| | Particle A5 | — | — | — | — | 1.0 | — |

TABLE 19

| Sunscreens | | Formulation Example | | | | | |
|---|---|---|---|---|---|---|---|
| | | 37 | 38 | 39 | 40 | 41 | 42 |
| Ingredients (wt %) | Sorbitan manoisostearate | 1.0 | 1.0 | 1.0 | 1.0 | 1.0 | 1.0 |
| | Polyether-modified silicone mixture | 5.0 | 5.0 | 5.0 | 5.0 | 5.0 | 5.0 |
| | Volatile silicone | 15.0 | 15.0 | 15.0 | 15.0 | 15.0 | 15.0 |
| | Isohexadecane | 5.0 | 5.0 | 5.0 | 5.0 | 5.0 | 5.0 |
| | Di(phytosteryl isostearyl cetyl stearyl behenyl) dimer dilinoleate | 0.2 | 0.2 | 0.2 | 0.2 | 0.2 | 0.2 |
| | Octyl p-methoxycinnamate | 5.0 | 5.0 | 5.0 | 5.0 | 5.0 | 5.0 |
| | Diethylaminohydroxybenzoyl hexyl benzoate | 1.0 | 1.0 | 1.0 | 1.0 | 1.0 | 1.0 |
| | Squalane | 3.0 | 3.0 | 3.0 | 3.0 | 3.0 | 3.0 |
| | Purified water | 43.6 | 43.6 | 43.6 | 43.6 | 43.6 | 43.6 |
| | Ethanol | 10.0 | 10.0 | 10.0 | 10.0 | 10.0 | 10.0 |
| | Finely divided titanium oxide | 3.0 | 3.0 | 3.0 | 3.0 | 3.0 | 3.0 |
| | Finely divided zinc oxide | 3.0 | 3.0 | 3.0 | 3.0 | 3.0 | 3.0 |
| | Titanium oxide | 1.0 | 1.0 | 1.0 | 1.0 | 1.0 | 1.0 |
| | Trimethylsiloxysilicic acid | 3.0 | 3.0 | 3.0 | 3.0 | 3.0 | 3.0 |
| | Phenoxyethanol | 0.2 | 0.2 | 0.2 | 0.2 | 0.2 | 0.2 |
| | Particle A1 | 1.0 | — | — | — | — | — |
| | Particle A2 | — | 1.0 | — | — | — | 0.5 |
| | Particle A3 | — | — | 1.0 | — | — | — |
| | Particle A4 | — | — | — | 1.0 | — | 0.5 |
| | Particle A5 | — | — | — | — | 1.0 | — |

The invention claimed is:

1. Hydrophobic alginic acid particles obtained by hydrophobizing a polyvalent metal salt of alginic acid using at least one hydrophobizing agent, wherein the hydrophobic alginic acid particles comprise ion-crosslinked polyvalent metal ions, the at least one hydrophobizing agent is at least one selected from the group consisting of salts of carboxylic acids, salts of amino acids, salts of amino acid derivatives, salts of sulfate esters, salts of sulfonic acids, and salts of phosphate esters, the at least one hydrophobizing agent gives rise to ion exchange with at least some of the ion-crosslinked polyvalent metal ions, accompanied by chemical bonding with the at least one hydrophobizing agent, the particles have a water absorption per 100 g of particles and an oil absorption per 100 g of particles such that the water absorption is lower than the oil absorption, and letting SD1, SD2 and SD3 be the respective percent transmittances to 560 nm wavelength light of a dispersion prepared by dispersing the hydrophobic alginic acid particles in a 3 wt % aqueous solution of sodium chloride to a concentration of 0.1 wt % when 72 hours, 240 hours and 720 hours have elapsed following preparation, and letting WD1, WD2 and WD3 be the respective percent transmittances to 560 nm wavelength light of a dispersion prepared by dispersing the hydrophobic alginic acid particles in water to a concentration of 0.1 wt % when 72 hours, 240 hours and 720 hours have elapsed following preparation, at least one of the ratios WD1/SD1, WD2/SD2 and WD3/SD3 is 0.9 or less.

2. The hydrophobic alginic acid particles of claim 1, wherein the at least one hydrophobizing agent is at least one selected from the group consisting of the salts of the carboxylic acids, the salts of amino acids, and the salts of amino acid derivatives.

3. The hydrophobic alginic acid particles of claim 2, wherein the at least one hydrophobizing agent selected from the group consisting of the salts of carboxylic acid, the salts of amino acid, and the salts of amino acid derivatives each contain a monovalent metallic ion.

4. The hydrophobic alginic acid particles of claim 1, wherein the polyvalent metal is a metal salt that forms divalent ions.

5. The hydrophobic alginic acid particles of claim 4, wherein the metal salt that forms the divalent ions comprises calcium.

6. The hydrophobic alginic acid particles of claim 1 which, at 25° C., are insoluble in water and are soluble in a 3 wt % aqueous solution of sodium chloride.

7. The hydrophobic alginic acid particles of claim 1 which have an average particle size of 5 mm or less.

8. A cosmetic comprising the hydrophobic alginic acid particles of claim 1.

9. A paint comprising the hydrophobic alginic acid particles of claim 1.

10. A resin composition comprising the hydrophobic alginic acid particles of claim 1.

11. A molded or formed article comprising the hydrophobic alginic acid particles of claim 1.

12. An electronic material comprising the hydrophobic alginic acid particles of claim 1.

13. A sheet comprising the hydrophobic alginic acid particles of claim 1.

* * * * *